US011597942B2

(12) United States Patent
Yao et al.

(10) Patent No.: US 11,597,942 B2
(45) Date of Patent: Mar. 7, 2023

(54) AUTOTROPHIC NITROGEN FIXATION GENES AND AN AUTOTROPHIC NITROGENASE EXPRESSION CASSETTE FOR PLANTS AND USES THEREOF

(71) Applicant: Shanghai Academy of Agricultural Sciences, Shanghai (CN)

(72) Inventors: Quanhong Yao, Shanghai (CN); Rihe Peng, Shanghai (CN); Jianjie Gao, Shanghai (CN); Yongsheng Tian, Shanghai (CN); Bo Wang, Shanghai (CN); Lijuan Wang, Shanghai (CN); Xiaoyan Fu, Shanghai (CN); Zhenjun Li, Shanghai (CN); Hongjuan Han, Shanghai (CN); Jing Xu, Shanghai (CN); Fujian Zhang, Shanghai (CN); Wenhui Zhang, Shanghai (CN); Yongdong Deng, Shanghai (CN); Yu Wang, Shanghai (CN)

(73) Assignee: SHANGHAI ACADEMY OF AGRICULTURAL SCIENCES, Shanghai (CN)

( * ) Notice: Subject to any disclaimer, the term of this patent is extended or adjusted under 35 U.S.C. 154(b) by 0 days.

(21) Appl. No.: 17/147,794

(22) Filed: Jan. 13, 2021

(65) Prior Publication Data

US 2022/0064658 A1 Mar. 3, 2022

(30) Foreign Application Priority Data

Aug. 28, 2020 (CN) ......................... 202010883945.8

(51) Int. Cl.
*C12N 15/82* (2006.01)
*C12N 9/00* (2006.01)
*C12N 9/02* (2006.01)

(52) U.S. Cl.
CPC ....... *C12N 15/8261* (2013.01); *C12N 9/0095* (2013.01); *C12Y 118/06001* (2013.01)

(58) Field of Classification Search
CPC ............ C12N 15/8227; C12N 15/8261; C12Y 118/06001
See application file for complete search history.

(56) References Cited

PUBLICATIONS

Allen, R. S., et al. "Expression of 16 nitrogenase proteins within the plant mitochondrial matrix." Frontiers in plant science 8 (2017): 287 (Year: 2017).*

Wang, L., et al. "A minimal nitrogen fixation gene cluster from *Paenibacillus* sp. WLY78 enables expression of active nitrogenase in *Escherichia coli*." PLoS genetics 9.10 (2013): e1003865 (Year: 2013).*

(Continued)

*Primary Examiner* — Weihua Fan
(74) *Attorney, Agent, or Firm* — Hauptman Ham, LLP

(57) ABSTRACT

Autotrophic nitrogen fixation genes and an autotrophic nitrogenase expression cassette for plants and uses thereof are disclosed. Nitrogenase related genes of nitrogen fixation gene cluster from *Paenibacillus* sp. are specifically optimized by plant expression patterns through synthetic biology, to obtain autotrophic nitrogen fixation genes, which are then constructed into plant constitutive expression units. The expression units are assembled in a plant expression vector by isocaudarner cloning method and transformed into plants, thereby realizing autotrophic nitrogen fixation of the plants.

2 Claims, 10 Drawing Sheets

Specification includes a Sequence Listing.

pYB2082

(56) References Cited

PUBLICATIONS

"OptimumGeneTM Gene Design System" (www.genscript.com/codon-opt.html), snapshot of Aug. 11, 2020 at https://web.archive.org/web/20200811092956/https://www.genscript.com/codon-opt.html (Year: 2020).*
Sun, Q., et al. "Creation and validation of a widely applicable multiple gene transfer vector system for stable transformation in plant." Plant molecular biology 83.4 (2013): 391-404. (Year: 2013).*
Ivleva et al., Expression of Active Subunit of Nitrogenase via Integration into Plant Organelle Genome, PLOS One; DOI:10.1371/journal.pone.0160951; Aug. 16, 2016; 13 pgs.
Burén et al., Purification and In Vitro Activity of Mitochondria Targeted Nitrogenase Cofactor Maturase NifB, Frontiers in Plant Science, 2017, vol. 8: Article 1567; 37 pgs.
Allen et al., Expression of 16 Nitrogenase Proteins within the Plant Mitochondrial Matrix, Frontiers in Plant Science, Mar. 3, 2017, vol. 8: Article 287; 14 pgs.
Yang et al., Polyprotein Strategy for Stoichiometric Assembly of Nitrogen Fixation Components for Synthetic Biology, Proceedings of the National Academy of Sciences of the United States of America, Jul. 30, 2018, vol. 115: No. 36; pp. 8509-8517.
Yang et al., Reconstruction and Minimal Gene Requirements for the Alternative Iron-Only Nitrogenase in *Escherichia coli*, Proceedings of the National Academy of Sciences of the United States of America, Aug. 19, 2014, vol. 111: pp. 3718-3725.
Yang et al., Modular Electron-Transport Chains from Eukaryotic Organelles Function to Support Nitrogenase Activity, Proceedings of the National Academy of Sciences of the United States of America, Feb. 13, 2017, vol. 114: pp. 2460-2465.
Tobias et al., The N-End Rule in Bacteria, Science, Nov. 29, 1991, vol. 254: pp. 1374-1377.
Xiong et al., PCR-Based Accurate Synthesis of Long DNA Sequences, Nature Protocols, Jul. 13, 2006, vol. 1, No. 2; pp. 791-797.
Peng et al., A Direct and Efficient Page-Mediated Overlap Extension PCR Method for Gene Multiple-Site Mutagenesis, Appl Microbiol Biotechnol; 2006, vol. 73(1): pp. 234-240.
Willison et al., The Use of Metronidazole to Isolate Nif-Mutants of Rhodopseudomonas Capsulate, and the Identification of a Mutant with Altered Regulatory Properties of Nitrogenase, Journal of General and Applied Microbiology. 1982, vol. 128: pp. 3001-3010.
Burgess-Brown, Nicola A., et al.; Codon optimization can improve expression of human genes in *Escherichia coli*: A multi-gene study; Protein Expression and Purification; May 2008; 59(1): 94-102.
Liu, Xiaomeng, et al.; Combined Assembly and Targeted Integration of Multigene for Nitrogenase Biosynthetic Pathway in *Saccharomyces cerevisiae*; ACS Synthetic Biology, May 22, 2019, 8, 1766-1775.

* cited by examiner

19 CK

AUTOTROPHIC NITROGEN FIXATION GENES AND AN AUTOTROPHIC NITROGENASE EXPRESSION CASSETTE FOR PLANTS AND USES THEREOF

CROSS-REFERENCE TO RELATED APPLICATION

This application claims the benefit of priority of Chinese Patent Application No. 202010883945.8 filed on Aug. 28, 2020, the disclosure of which is incorporated by reference herein in its entirety.

TECHNICAL FIELD

The present application relates to the field of plant synthetic biology, and particularly to, autotrophic nitrogen fixation genes and an autotrophic nitrogenase expression cassette for plants and uses thereof.

INCORPORATION BY REFERENCE

The sequence listing provided in the file entitled Sequence_listing_2011204US_ST25_s.txt, which is an ASCII text file that was created on Dec. 31, 2020, and which comprises 69,897 bytes, is hereby incorporated by reference in its entirety.

BACKGROUND

Nitrogen is one of the most important components of living cells. 60% of total fixed nitrogen from all natural and industrial sources on the earth comes from biological nitrogen fixation (BNF), that is, $N_2$ in the atmosphere is converted to $NH_3$. However, BNF only occurs in a limited species of bacteria and archaea.

Plants cannot directly use $N_2$ in the atmosphere. Dependence of crop growth on $N_2$ has led to build many nitrogen fertilizer manufacturing plants in the world to meet its growth requirements, while only approximately 50% of the nitrogen fertilizer applied is used by plants, excessive nitrogen fertilizer has caused surface and groundwater pollution and soil acidification around the world, thereby endangering human health and sustainable agricultural development.

Scientists have always dreamed of cultivate plants that can be nitrogen-self-sufficient/semi-self-sufficient. With development of biotechnology, possibility of creating plants capable of authigenic nitrogen fixation has become increasingly clear. Currently, there are following two methods are mainly used for cultivating authigenic nitrogen-fixing plants.

The first method is through symbiotic interaction between non-legumes and nitrogen-fixing bacteria, so that the non-legumes form rhizobia that the same in legumes, then a symbiotic nitrogen fixation systems between the rhizobia and the legumes are formed by steps of: mutual recognition of the rhizobia to plants, successful infection of the rhizobia, formation of bacteroids, and establishment of relationship between nodulation and nitrogen fixation.

Therefore, at least three problems need to be solved to achieve symbiotic nitrogen fixation in the non-legumes: (1) the non-legumes should have signal transduction genes that recognize nodulation factors, (2) rhizobia should establish a stable interaction with plants, and (3) an anaerobic environment for nitrogen fixation is required. A plenty of evidence shows that the signal transduction genes that coexist with the rhizobia of the legumes are very conserved in non-legumes such as arbuscular plants and cereals. Through evolution, non-rhizobia may be transformed into strains that can initiate nodulation formation and new hosts infection, or can improve nodulation ability of the rhizobia. However, due to complexity of plant-microbe interactions, this method is extremely difficult to implement, and interaction mechanism between plants and azotobacter and their symbiotic characteristics must be fully revealed.

The second method is to directly introduce bacterial nitrogen fixation genes into plants, so that the plants express nitrogenase and fix nitrogen, and the nitrogenase further catalyzes nitrogen into ammonia.

It is known that the nitrogenase is composed of two components: one is an Fe protein containing a $\gamma 2$ homodimer, and the other is a MoFe protein involving an $\alpha 2\beta 2$ heterotetramer. Where the Fe protein is encoded by nifH, and the MoFe protein is encoded by nifDK. In addition to the genes for these two structural proteins, a dozen other nif genes are extremely conserved in free-living and symbiotic diazotrophs for the processing of nitrogenase metalloclusters and catalytic stability (nifMZ, nifW and nifUS) and the synthesis of a specific Mo cofactor (FeMo-co) bound to the MoFe protein (nifB, nifQ, nifENX and nifV), and so on.

Few studies have attempted to express the nitrogenase in plants. Ivleva et al. discloses that nifH and nifM genes are expressed in tobacco chloroplasts, and an active Fe protein can be detected, indicating that the chloroplasts can be used as a place for expression of the nitrogenase (Ivleva et al., PlosOne 2016, 11: e0160951). Buren et al. find that NifB protein as a cofactor at the active site of the nitrogenase provides a key metal cluster intermediate NifB-co, which can be expressed in tobacco and accumulate as a soluble protein, and participated in FeMo-co synthesis in vitro (Buren et al., Frontiers in Plant Science, 2017, 8: 1567). Allen et al. find that 16 Nif proteins required in the formation of the nitrogenase in *Klebsiella pneumoniae* can be individually expressed and targeted to mitochondria in tobacco (Allen et al., Frontiers in Plant Science, 2017, 8: 00287).

The minimum number of nif genes required to produce a functional nitrogenase in plants and the optimal expression levels of various genes required to produce a high-efficiency nitrogenase are still unknown. Yang et al. construct fourteen gene systems with five fusion genes such as nifHǒDǒK, nifEǒN~B, nifUǒS, nifJǒVǒW and nifFǒMǒY; which exhibit 72% nitrogenase activity, and an obtained *Escherichia coli* transformants could use $N_2$ as the sole nitrogen source and grow slowly (Yang et al., Proceedings of the National Academy of Sciences of the United States of America, 2018, 115: 8509-8517). Yang et al. also construct a minimal FeFe nitrogenase system including 10 proteins required to sustain nitrogen fixation in *E. coli* (Yang et al., Proceedings of the National Academy of Sciences of the United States of America, 2014, 111: 3718-3725). Among 10 proteins required by the microbial nitrogen fixation system, the bacterial electron transfer system encoded by nifJ and nifF could be functionally replaced by plant-sourced electron transport chain (Yang et al., Proceedings of the National Academy of Sciences of the United States of America, 2017, 114: 2460-2465).

In addition, NifU and NifS are involved in the assembly of iron-sulfur cofactors, and can be substituted in the mitochondria of yeast or tobacco. NifV, which catalyzes the formation of homocitrate, may be produced by some eukaryotes. Thus, in theory, as long as six microbial core proteins such as NifB, NifE, NifN, NifH, NifD, and NifK are expressed, a nitrogen-fixing plant could be developed.

Currently, most studies have focused on the expression of nitrogenase in plant mitochondria which contains many oxygen-consuming enzymes to allow oxygen-sensitive enzymes play a role. Expression of Nif protein in the mitochondria is a serious challenge because transit peptides that precisely targets protein to the mitochondria may affect accumulation of the Nif protein, the goal of directly introducing nitrogen fixation gene (hereafter referred to as nif, herein the term "nitrogen fixation gene" and "nif" are used interchangeably) into plants has not been achieved.

SUMMARY

Some embodiments of the present application provide autotrophic nitrogen fixation genes and an autotrophic nitrogenase expression cassette for plants and uses thereof. Nitrogenase related genes of nitrogen fixation gene cluster from *Paenibacillus* sp. are specifically optimized by plant expression patterns through synthetic biology, to obtain the autotrophic nitrogen fixation genes, which are then constructed into plant constitutive expression units one by one. The expression units are assembled in a plant expression vector by isocaudarner cloning method and transformed into plants, thereby realizing autotrophic nitrogen fixation of the plants.

In an embodiment of the present application, it is provided autotrophic nitrogen fixation genes for plants, including nitrogen fixation genes nifB, nifE, nifN, nifH, nifD and nifK derived from nitrogen-fixing bacteria and optimized by plant expression patterns.

Optionally, the nitrogen-fixing bacteria is *Paenibacillus* sp, and the autotrophic nitrogen fixation genes further include nifV, nifX and HesA optimized by the plant expression patterns.

Optionally, optimized by the plant expression patterns includes steps of: optimizing genes based on plant preferred codons; eliminating recognition sites of commonly used restriction enzyme in the genes; eliminating reverse repeat sequences, stem loop structure and transcription termination signal to keep GC/AT balance in the genes; eliminating intron recognition sequences; making protein encoded by the genes conform to N-terminal principle; avoiding using CG and TA double oligonucleotides at positions 2 and 3; and increasing free energy of 5' end of the genes and decreasing free energy of 3' end of the genes.

Optionally, nucleotide sequences of the nitrogen fixation genes nifB, nifE, nifN, nifH, nifD, nifK, nifV, nifX and HesA optimized by the plant expression patterns are shown in SEQ ID No. 1, SEQ ID No. 2, SEQ ID No. 3, SEQ ID No. 4, SEQ ID No. 5, SEQ ID No. 6, SEQ ID No. 7, SEQ ID No. 8, and SEQ ID No. 9, respectively.

Optionally, the nitrogen fixation genes optimized by the plant expression patterns are expressed in cytoplasm.

In another embodiment of the present application, it is further provided an autotrophic nitrogen fixation gene expression unit for plants, which is composed of one nitrogen fixation gene optimized by the plant expression patterns as described above, and a CaMV35SΩ promoter and a NOS terminator.

Optionally, in each autotrophic nitrogen fixation gene expression unit, restriction sites of EcoRI and XhoI are added to 5' domain, and restriction sites of SalI and HindIII are added to 3' domain.

Optionally, in each autotrophic nitrogen fixation gene expression unit, the nitrogen fixation gene optimized by the plant expression patterns is selected from nucleotide sequences as shown in SEQ ID NO.1, SEQ ID NO.2, SEQ ID NO.3, SEQ ID NO.4, SEQ ID NO.5, SEQ ID NO.6, SEQ ID NO.7, SEQ ID NO.8, or SEQ ID NO.9.

In another embodiment of the present application, it is further provided an autotrophic nitrogenase expression cassette for plants, including nine autotrophic nitrogen fixation genes expression units as described above, and the autotrophic nitrogen fixation genes include nitrogen fixation genes nifB, nifE, nifN, nifH, nifD, nifK, nifV, nifX, and hesA optimized by the plant expression patterns as described above. And restriction sites of EcoRI and XhoI are added to 5' domain and restriction sites of SalI and HindIII added to 3' domain in each of the autotrophic nitrogen fixation gene expression units.

Optionally, in the autotrophic nitrogenase expression cassette, each of the autotrophic nitrogen fixation gene expression units is completely inserted into a plant expression vector by isocaudarner cloning method.

Optionally, the expression cassette segment of reporter gene in an original plant expression vector is deleted from the plant expression vector, and fragments of multiple cloning sites in the original plant expression vector are replaced by EcoRI, SalI, BamHI, KpnI, XbaI and HindIII.

Optionally, the plant expression vector contains a resistance selection marker.

In another embodiment of the present application, it is further provided use of the autotrophic nitrogenase expression cassette for autogenic nitrogen fixation in plants.

In an embodiment of the present application, the autotrophic nitrogenase expression cassette is transformed into plants to obtain plant material, the plant maternal is capable of assembling nitrogenases in cells successfully, and then nitrogen in air is converted into ammonia by nitrogenase, thereby realizing autotrophic nitrogen fixation of the plants.

The present application selects a compact BNF system from *Paenibacillus* to design and construct nitrogen fixing plants. Herein *Paenibacillus* are facultative anaerobic or strictly aerobic bacteria, its nitrogen fixation gene cluster consists of nine genes, including the nitrogen fixation genes nifB, nifE, nifN, nifH, nifD, and nifK contained in all nitrogen-fixing bacteria, and which encode accessory proteins nifV, nifX, and hesA required for optimal nitrogenase activity. In order to efficiently express a stable nitrogenase, the present application designs to express the nitrogenase in cytoplasm rather than in different organelles.

In the present application, after all genes involved in assembly of the nitrogenase in the nitrogen fixation genes cluster of the nitrogen-fixing bacteria are modified, the CaMV35SΩ promoter is used to control the expression of all the genes, to construct plant constitutive expression units. Then all nine genes expression units that encoding bacterial nitrogenase subunits and its accessory proteins are constructed into a plant expression vector by synthetic biological technology. Finally, the plant expression vector is transformed into plants cells by *Agrobacterium* mediated transformation method, so that the nitrogenase is expressed in the cytoplasm and then cultivated plants that can convert nitrogen into ammonia.

The present application uses gene optimization and synthesis methods to optimize and synthesize all nine genes of the nitrogen fixation genes cluster in accordance with plant preference codons and structural stability principles. When optimizing the nitrogen fixation genes based on the plant expression patterns, the genes are optimized by the plant preference codes to improve gene translation efficiency, recognition sites of commonly used restriction enzyme in the genes are eliminated to facilitate construction of expression cassette. Reverse repeat sequences, stem loop structure and transcription termination signal are eliminated to keep GC/AT balance in the genes and improve the stability of RNA. Intron recognition sequences are eliminated to avoid intron splicing in coding region, thereby leading to loss of gene function. Proteins encoded by the genes are conformed to N-terminal principle to improve stability of the translated proteins. CG and TA double oligonucleotides are not used at positions 2 and 3 to avoid causing methylation of the genes in plants, thereby leading gene silence. Free energy of 5'end of the genesis designed to increase and free energy of 3' end is designed to decrease, to improve the genes translation efficiency.

In the present application, gene nifH encodes γ subunit of the nitrogenase, and its homodimer forms Fe protein of the nitrogenase; gene nifD encodes a subunit of the nitrogenase, which is an important part of the MoFe protein of the nitrogenase, it forms a heterotetramer $\alpha 2\beta 2$ with β subunit; gene nifK encodes β subunit of the nitrogenase; genes nifB, nifE, nifN, nifX, hesA and nifV encode accessory proteins of the nitrogenase.

The present application uses long gene synthesis technology to synthesize full-length sequence of each gene, and based on optimization requirements for the nitrogen fixation genes, primers are designed for each of optimized nitrogen fixation genes. When synthesizing, the amount of middle primer is added less, and the amount of outer primer is added more, so as to reduce synthesis of small middle fragments and obtain more full-length gene fragments. In case of gene mutation, error correction will be performed according to multi-sites mutation technology. After optimization, each synthetic gene is spliced with CaMV35SΩ promoter and NOS terminator separately, and controlled by the CaMV35SΩ promoter and the NOS terminator to construct an expression unit.

Due to the existence of a large number of repetitive sequences in the promoter and terminator, under normal circumstances, homologous recombination cloning methods cannot assemble all gene expression units into one vector. The present application uses an improved isocaudarner cloning method to construct plant expression vector of the nitrogenase. Restriction sites EcoRI and XhoI are added to the 5' domain of each expression unit, while restriction sites SalI and HindIII are added to the 3' domain, and all expression units of the genes are inserted into the plant expression vector.

The present application has at least following advantages.

1) The present application integrates the coding genes of bacterial nitrogenase subunits and their assembly related proteins into plant chromosomes after reconstruction, so that the plants can be stably expressed and then assembled into nitrogenases with nitrogen fixing activity in cells, thereby realizing autotrophic nitrogen fixation in the plants for the first time.

2) When constructing the expression cassette of the nitrogenase, the present application uses the isocaudarner cloning method to add EcoRI and XhoI sites to 5' domain of each gene expression unit, while add SalI and HindIII to 3' domain, and then design primers for splicing, so that expression units of each nitrogen fixation genes are successfully constructed on the same expression vector, to stable connection and not easily to break.

3) The transgenic plants transformed with the autotrophic nitrogen fixation of the present application can efficiently produce various Nif proteins. The functional activity of the nitrogenase in plants can be detected by acetylene reduction method in vitro and $^{15}N_2$ incorporation method. Compared with the wild-type plants (i.e., plants that have not been transformed with the autotrophic nitrogen fixation genes), the content of $\delta^{15}N$ ‰ in the autotrophic nitrogen fixation plants of the present application is increased by more than 30 times.

DETAILED DESCRIPTION

Figure 1:
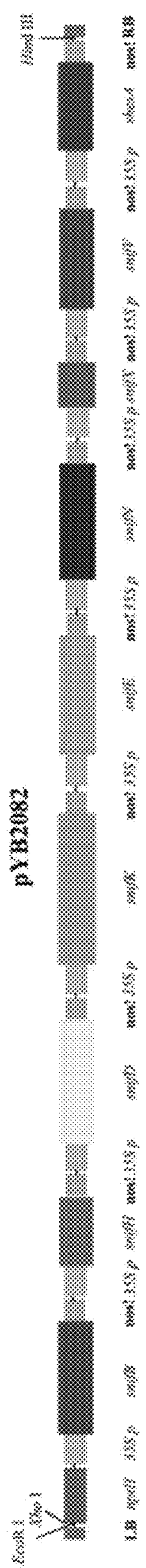
FIG. 1 shows a construction map of the plant autotrophic nitrogenase expression vector pYP2082 in example 2 of the present application.

The present application will be further described below with reference to specific examples.

Blunt terminus cloning vectoris purchased from TaKaRa BioTechnology (Dalian) Co., Ltd. KOD FX Taq enzyme from Toyobo Biotech Co., Ltd. of Japan.

Example 1 Optimization and Synthesis of Autotrophic Nitrogen Fixation Genes for Plants Nitrogen fixation genes in the nitrogen fixation gene cluster from *Paenibacillus* sp. (GenBank accession number CP017967.3) are optimized.

The nitrogen fixation genes are optimized based plant expression patterns, including: the genes are optimized based on plant preference codons to improve gene translation efficiency; recognition sites of commonly used restriction enzyme in the genes are eliminated to facilitate construction of expression cassette; reverse repeat sequences, stem loop structure and transcription termination signal are eliminated to keep GC/AT balance in the genes and improve the stability of RNA; intron recognition sequences are eliminated to avoid intron splicing in coding region, thereby leading to loss of gene function; protein encoded by the genes is conformed to N-terminal principle (Science, 1991, 254: 1374-1377) to improve stability of the translated proteins; 6 or more consecutive A+T sequences and 5 or more G+C sequences are avoid; CG and TA double oligonucleotides are not used at positions 2 and 3 to avoid causing methylation of the genes in plants, thereby leading the genes is silenced; free energy of 5'end of the genes is designed to increase and free energy of 3' end is designed to decrease, to improve the gene translation efficiency.

Primers for each of the nitrogen fixation genes are synthesized according to the optimization method described above. Full-length genes are synthesized by using long gene synthesis technology (Nature Protocol, 2006, 1(2): 791-797), addition amount of each middle primer (i.e., remaining primers except the primers on both sides of the head and tail) is 2 ng, addition amount of each outer primer is 30 ng, and amplification conditions are: 94° C. for 30 s; 50° C. for 30 s; 72° C. for 2 min; a used Taq DNA polymerase is KOD FX taq enzyme; 25 cycles.

PCR product is recovered with 1% agarose gel, and 10 μl of the PCR product is directly connected to blunt terminus cloning vector, overnight at 4° C., and then which are efficiently transformed into DH5α competence to obtain a positive clone, sequence is determined, In case of mutation in the synthesized gene, error correction will be carried out according to multi-sites mutation technology (Appl Microbiol Biotechnol. 2006, 73(1): 234-240). Nucleotide sequences of the nine synthesized autotrophic nitrogen fixation genes are shown in SEQ ID NO.1 to 9.

Specific primers designed to optimize all nine nitrogen fixation genes are as follows: primers designed to optimize the gene nifH are shown in nucleotide sequence SEQ ID NO.10 to 31; primers designed to optimize the gene nifD are shown in nucleotide sequence SEQ ID NO.32 to 67; primers designed to optimize the gene nifK are shown in nucleotide sequence SEQ ID NO.68 to 105; primers designed to optimize the gene nifB are shown in nucleotide sequence SEQ ID NO.106 to 142; primers designed to optimize the gene nifE are shown in nucleotide sequence SEQ ID NO.143 to 176; primers designed to optimize the gene nifN are shown in nucleotide sequence SEQ ID NO.177 to 208; primers designed to optimize the gene nifX are shown in nucleotide sequence SEQ ID NO.209 to 218; primers designed to optimize the gene hesA are shown in nucleotide sequence SEQ ID NO.219 to 237; primers designed to optimize the gene nifV are shown in nucleotide sequence SEQ ID NO.238 to 265.

Example 2 Construction of an Autotrophic Nitrogenase Expression Cassette for Plants The nine synthesized autotrophic nitrogen fixation genes of example 1 are used to construct autotrophic nitrogen fixation genes expression units for plants respectively, where CaMV 35S Ω promoter and NOS terminator are used for expression control. Each of the genes is seamlessly connected to the promoter and the terminator by using multi-gene overlap extension technology, and then all the expression units are inserted into a plant expression vector pYP674 in a step-by-step manner.

Due to the existence of a large number of repetitive sequences in the promoter and terminator, the traditional homologous recombinant cloning method cannot be used to assemble all genes expression units into one vector. Therefore, the present application adopts an improved restriction enzyme cloning method to construct autotrophic nitrogenase expression vector for plants.

EcoRI and XhoI sites are added to the 5' domain of the expression unit of each gene, while SalI and HindIII are added to the 3' domain. Then all genes expression units are inserted into a plant expression vector, respectively. The vector is modified by deleting expression cassette segment of the reporter gene and replacing polyclonal site fragment with EcoRI, SalI, BamHI, KpnI, XbaI and HindIII. Herein the insertion of all the expression units does not require a specific order, and after each expression unit is inserted, enzyme digestion with EcoRI and HindIII and DNA sequencing were performed to ensure cloning accuracy, and finally an autotrophic nitrogenase expression vector for plants is obtained.

In this example, a plant expression vector named pYP674 derived from expression vector pCAMBIA-1301 is used, in which expression cassette segment of the reporter gene UidA is deleted and the polyclonal site fragment is replaced by EcoRI, SalI, BamHI, KpnI, XbaI and HindIII. The expression units are gradually inserted into the plant expression vector with an order of each gene in the nitrogen fixation genes cluster of *Paenibacillus*. Following insertion of each expression unit, enzyme digestion with EcoRI and HindIII and DNA sequencing are performed to ensure cloning accuracy. Finally an autotrophic nitrogenase expression vector for plants named pYP2082 is obtained, it construction map is shown in FIG. 1.

Herein primers at both ends for constructing the expression units are shown in SEQ ID NO.266 to 267. When constructing the expression units, each of the autotrophic nitrogen fixation genes in example 1 is spliced with the CaMV35SΩ promoter and the NOS terminator, and splicing primers are shown in SEQ ID NO.268 to 269.

When constructing the autotrophic nitrogenase expression cassette, splicing primers for the expression unit of the nitrogenase γ subunit gene nifH are shown in the nucleotide sequences SEQ ID no. 270-273; splicing primers for the expression unit of the nitrogenase a subunit gene nifD are shown in the nucleotide sequences SEQ ID NO.274 to 277; splicing primers for the expression unit of the nitrogenase β subunit gene nifK are shown in the nucleotide sequences SEQ ID NO.278 to 281; splicing primers for the expression unit of the gene nifB are shown in the nucleotide sequences SEQ ID NO.282 to 285; splicing primers for the expression unit of the gene nifE are shown in the nucleotide sequences SEQ ID NO.286 to 289; splicing primers for the expression unit of the gene nifN are shown in the nucleotide sequence SEQ ID NO.290 to 293; splicing primers for the expression unit of the gene nifX are shown in the nucleotide sequences SEQ ID NO.294 to 297; splicing primers for the expression unit of the gene hesA are shown in the nucleotide sequences SEQ ID NO.298 to 301; splicing primers for the expression unit of the gene nifV are shown in the nucleotide sequences SEQ ID NO.302 to 305.

Example 3 Cultivation of *Agrobacterium* and Transformation of Plants

The autotrophic nitrogenase expression vector pYP2082 for plants prepared in example 2 is transformed into *Agrobacterium* by electroporation. A single strain is picked and cultured in 25 ml YEB medium (50 mg/L rifampicin) overnight, then 5 ml bacterial solution is transferred to 100 ml YEB medium (50 mg/L rifampicin), and incubated until $OD_{600}$=0.7-0.8. Then the bacterial solution is placed on ice for 10 min, centrifuged at 5000 rpm for 10 min, collected the bacterial and added 100 ml sterile double distilled water to wash twice.

Following the bacterial is suspended with 4 ml of 10% glycerol, transferred to a 50 ml centrifuge tube, centrifuged with 5500 rpm for 10 min at 4° C., then the bacterial is collected. The collected bacterial is suspended with 500 μl of 10% glycerol, transferred to a 1.5 ml centrifuge tube, 70 μl of competent cells are taken, to which add 1 μl plasmid pYP2082, and mix with a yellow pipette tip without tip, then transfer to a 0.1 cm electric shock cup.

Electric shock parameters: 200 Ω, 1.7 KV, 2.5 F. 800 μl SOC culture medium is added immediately after electric shock, and incubated for 1 hour, then 100 µl is taken to apply resistant plate to screen transformants, and incubated at 28° C.

1) Screened Transformants is Transformed into Rice According to Following Method.

N6 medium is used as a basic medium, after hulled seeds is pollinated, 12-15 days of immature embryos are surface-disinfected and then inoculated into N6D2 medium to induce callus. After cultivated 4-7 days, the callus is taked and transformed. Here the N6D2 medium is prepared as follows: 500 mg/L casein, 30 g/L sucrose, 2 mg/l 2,4-Dichlorophenoxyacetic acid, and 2.5 g/L Phytagel are added to the N6 medium, pH=5.8.

After the transformants is cultured to OD=0.8~1.0, centrifuged at 5000 g for 8 minutes and washed once with $ddH_2O$. Following it is infected with an equal volume of MS medium for 8 minutes, sucked up and placed in a medium containing MS, 1 mg/LNAA and 2 mg/L BA, then cultured at 22° C. for 3 days. It is transferred to a selection medium (N6 medium with 500 µg/ml of cephalosporin Cb and 50 µg/ml hygromycin HAT), transformed callus are cultured on a resistant medium containing hygromycin for 3-4 generations, pale yellow embryogenic callus is transferred to differentiation medium (N6 medium with 2 mg/L KT, 500 µg/ml Cb and 50 µg/ml hygromycin HAT) for differentiation culture, sprouts are differentiated for about 30 days, light intensity is 1500-2000 1×, 12-14 h/d, the sprouts grow to 2 mm and transfer to a rooting medium (containing ½ MS and 0.5 mg/L IBA) for rooting culture. Herein 500 mg/L casein acid hydrolysate (CH), 0-700 mg/L glutamine or arginine, 30-80 g/L sucrose, and 6 g agar are added to the above mediums, pH 5.8, subculture cycle is 25 days.

Transgenic rice obtained above (herein after referred to as transgenic plant) is planted in field, and seeds are collected. The seeds are screened with MS medium containing hygromycin HAT (50 µg/ml), and screened resistant seeds are subjected to molecular identification. Total DNA of leaves are extracted and with reference to methods of "Molecular Cloning", specific primers are designed by using hygromycin resistance gene HPT to perform PCR analysis for the transgenic plants, in order to prove whether the target gene is introduced at molecular level. More than 30 independent transgenic plants are obtained.

Here PCR amplified conditions are: 94° C. for 30 s, 60° C. for 30 s, 72° C. for 4 min, 25 cycles.

2) *Arabidopsis* is Transformed According to the Following Floral Dip.

A single *Agrobacterium* strain containing the autotrophic nitrogenase expression vector pYB2082 is inoculated into 5 ml LB medium with corresponding antibiotics and cultured at 28° C. for 2 days, then 5 ml of bacterial solution is transferred to 500 ml of liquid LB medium at 28° C. for culturing 16-24 hours (OD=1.5-2.0), the bacterial solution obtained may store at 4° C. for 30 days.

Bacterial cells are collected at room temperature and centrifuged at 4000 g for 10 minutes, an equal volume of 5% fresh sucrose solution is added to suspend, then 0.02% Silwet-77 is added with mixing and transferred to a beaker. Each strain is transformed with 300 ml to obtain 2-3 pots cell, and transformed again after 7 days. *Arabidopsis* is placed upside down and immersed in the bacterial solution for 10 seconds. Both rosette and inflorescence are infected, the bacterial solution of the transgenic plant is dried in air for 3-5 seconds after infection. The transgenic plant is surrounded with a plastic wrap and placed flat for 16-24 hours, the transformed plants cannot place under high temperature and strong light. The plastic wrap is opened and maintains certain humidity. After one month of growth, seeds are harvested. 50 µg/mL hygromycin is used to screen transformed plants, more than 30 independent transformed plants are obtained.

Example 4 PCR Detection of Autotrophic Nitrogen Fixation Gene in the Transgenic Plants The total DNA is extracted from leaves of the transgenic plants by CTAB method. Three plants with good germination and growth well are randomly selected for PCR identification of the target gene. Wild-type (i.e., non-transgenic) plant is used as a negative control, and the constructed autotrophic nitrogenase plant expression vector pYP2082 is used as a positive control.

Specific primers for the optimized 9 autotrophic nitrogen fixation genes nifB, nifH, nifD, nifK, nifN, nifE, nifV, nifX and HesA in example 1 are used to identify each gene in the transgenic plant by PCR.

Figure 2:
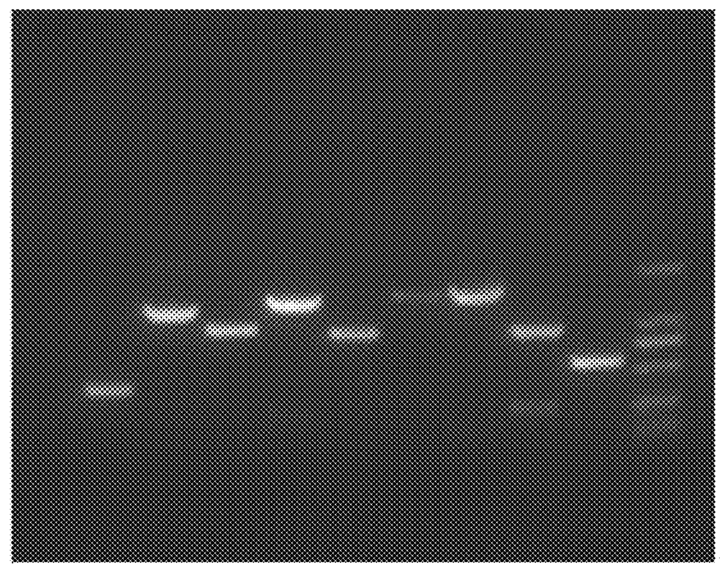
FIGS. 2-3 show PCR detection results of the autotrophic nitrogen fixation genes in plants in example 4 of the present application.
Figure 3:
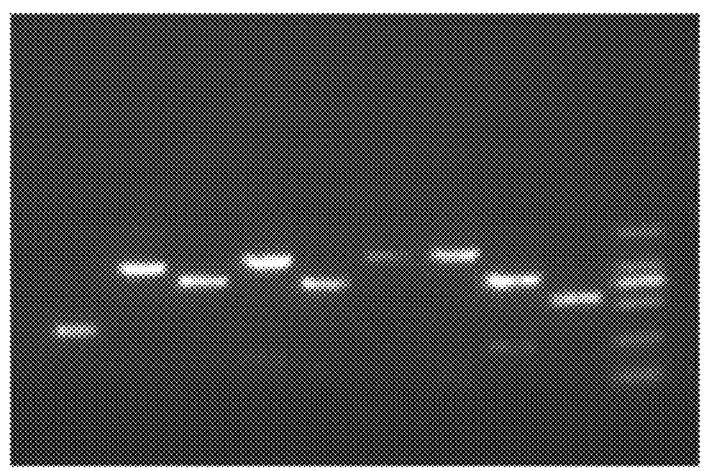
Figure 4:
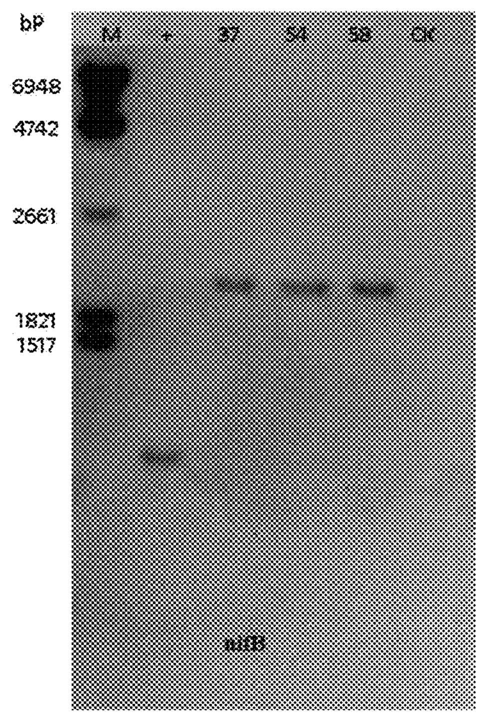
FIGS. 4-12 show Northern detection results of the autotrophic nitrogen fixation genes in plants in example 5 of the present application.
Figure 5:
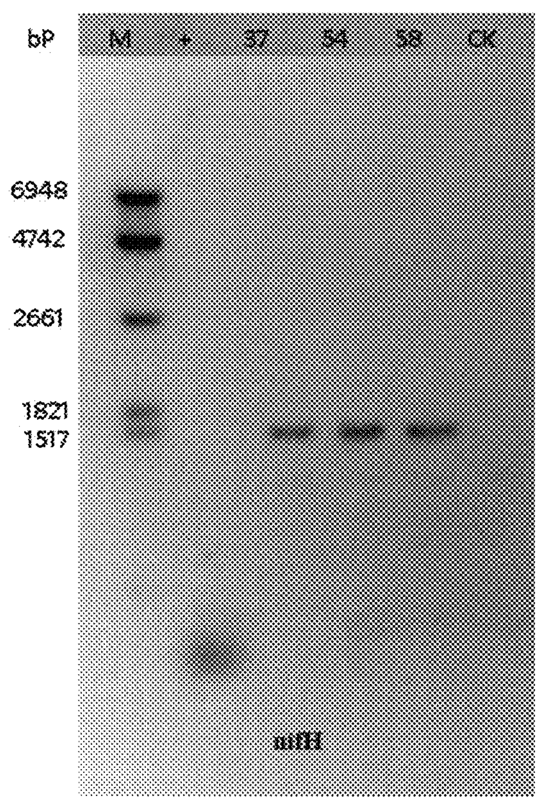
Figure 6:
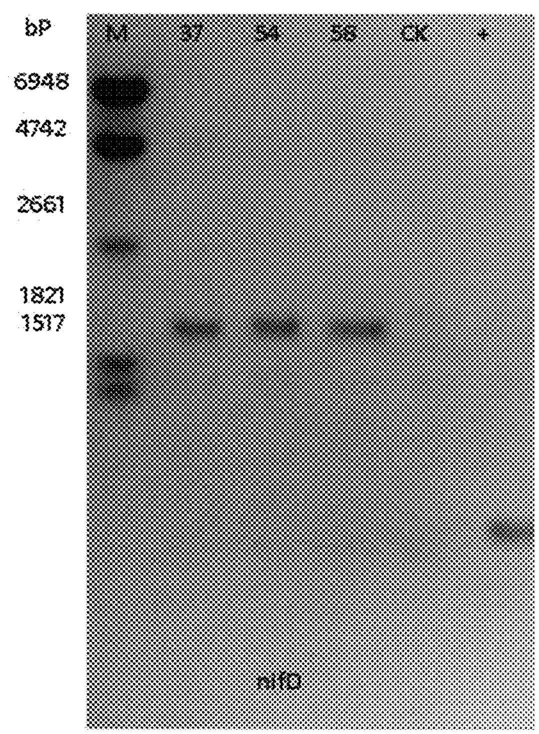
Figure 7:
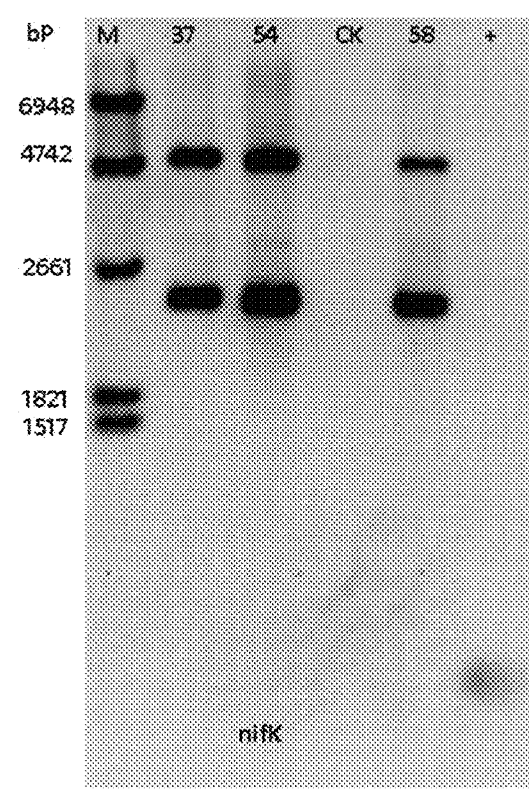
Figure 8:
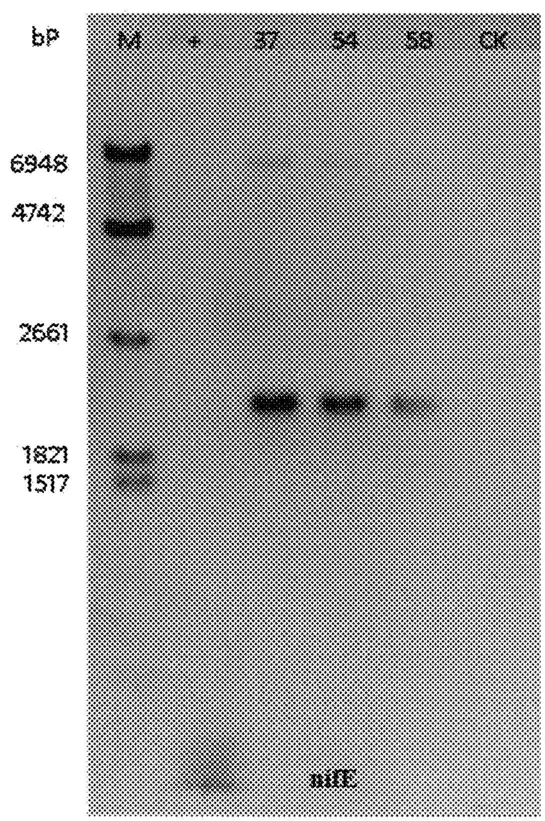
Figure 9:
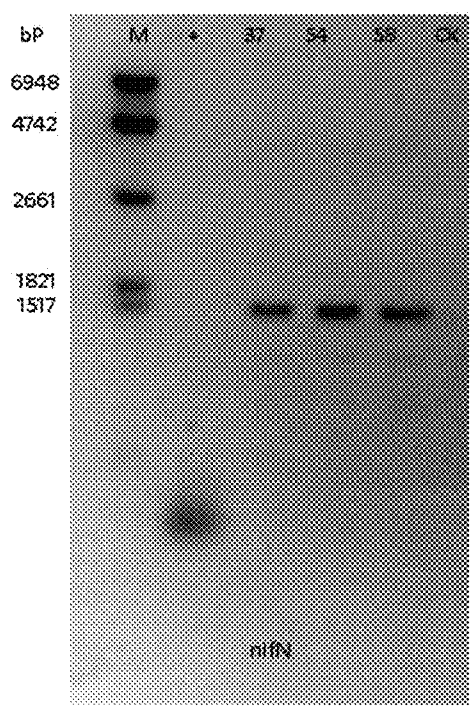
Figure 10:
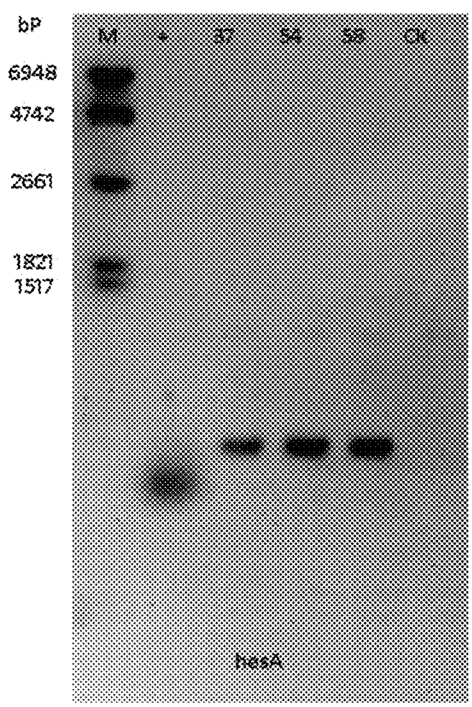
Figure 11:
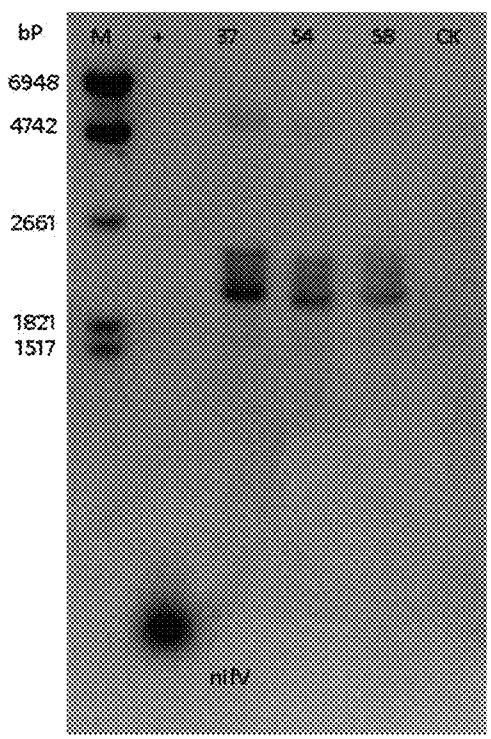
Figure 12:
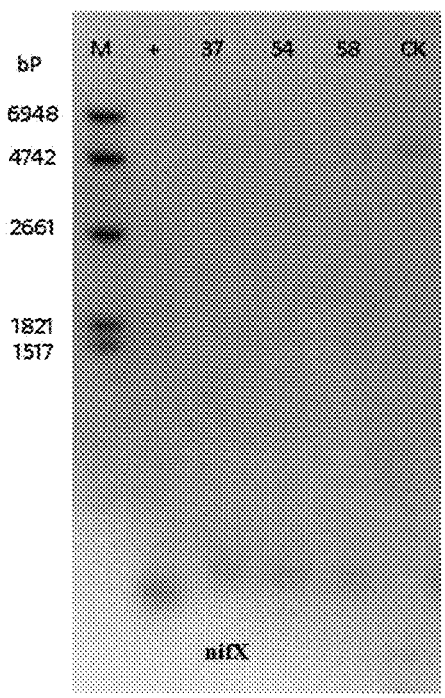

PCR amplification conditions are: 94° C. for 30 s; 60° C. for 30 s; 72° C. for 2 min; and 25 cycles of the amplification. 2 µl PCR product is taken to perform electrophoresis with 1% agarose gel, the results are shown in FIGS. 2-3. FIG. 2 shows PCR result of each autotrophic nitrogen fixation gene in the transgenic rice, and FIG. 3 shows PCR result of each autotrophic nitrogen fixation gene in the transgenic plant *Arabidopsis*, where letters X, V, N, K, H, E, D, B, and A represent the genes nifX, nifV, nifN, nifK, nifH, nifE, nifD, nifB and HesA, respectively. M is 2 KD DNA molecular weight marker.

It is seen from FIG. 2, all the genes hesA (A), nifB (B), nifH (H), nifD (D), nifK (K), nifN (N), nifE (E), nifV (V), and nifX (X) can be amplified by the specific primers in the transgenic rice and *Arabidopsis.*

Example 5. Analysis Expression of Each Gene in the Transgenic Plants by Northern Blotting Total RNA (sample) is extracted from seeding of the transgenic plants by using RNA Extraction Kit provided by Shenggong Bioengineering Co., Ltd. (Shanghai, China) according following protocol.

1 ml Trizol reagent is added to the sample, and tissue block volume of the sample is controlled not exceed 10% of volume of Trizol. It is pipetted repeatedly with a pipette, an obtained homogenate is placed at room temperature for 5 min until nucleic acid and protein therein are fully dissociated. 0.2 ml chloroform is added into the homogenate, lid of the sample tube is closed tightly, shake violently by hand for 15 s, then put it stand at room temperature for 2-3 mins, later centrifuge with 10000 g for 10 min at 4° C.

Carefully transfer upper water phase (colorless) into a new test tube, meanwhile calculate volume of water phase taken and add the same volume isopropanol to the tube, close the tube cap tightly and shake it gently. The tube is placed at room temperature for ten minute, after RNA is fully precipitated, centrifuge with 10000 g for 10 min at 4° C.

Discard the supernatant and keep the precipitate, add 1 ml of 75% alcohol to the tube to wash the precipitate. Then close the tube cap tightly and shake it gently. To remove residual isopropanol and salt by centrifuge the tube with 7500 g for 5 min at 4° C., then open the tube cap, discard the supernatant, and dry RNA precipitate at room temperature or under vacuum, and then dissolve the RNA precipitate with RNase-free water, RNA electrophoresis is performed with 1% agarose gel.

The RNA electrophoresis and trans-membrane are performed according to following methods.

The electrophoresis tank is washed with detergent and rinsed with deionized water, dried with ethanol, filled with 3% $H_2O_2$ solution and placed at room temperature for 10 min, then the bath is rinsed with DEPC water. Sample is electrophoresed in 1×MOPS buffer, before loading the sample, pre-electrophoresis at 80V for 5-15 min to let the sample enter the gel quickly, and electrophoresis at 50-60V for 2 h. Then electrophoresis gel is washed by 0.1% DEPC water to remove formaldehyde, dipped in 20×SSC buffer 45 min. A salt bridge is built by using a thick filter paper, added another filter paper infiltrated with 20×SSC buffer to remove air bubbles. The gel is placed to face up the center of the filter paper, upper left corner of the gel is cutted off as a mark, then all around of the gel is sealed with a plastic film to prevent short circuit. After a nylon membrane having the same size as the gel is infiltrated with 20×SSC buffer and then placed on the gel, cut off a corner to mark it. Two pieces of the filter paper having the same size as the gel is placed on the nylon membrane and infiltrated with 20×SSC buffer to remove air bubble. A stack of absorbent paper is placed on the filter paper, then added 0.5 kg weight on the paper. The trans-membrane is performed for 18 h.

A probe is prepared by PCR. 500 ng (1 μl) of reverse transcription cDNA fragment and 7.5 ng (0.5 μl) of forward and reverse primers for each optimized gene are mixed in 0.5 ml Eppendorf tube, boiled in water for 5 min and immediately placed on ice for 1 min, and then added 5 μl PCR DIG probe synthesis mix, 5 μl PCR reaction buffer, 0.8 μl PCR Enzymemix, 37.2 μl $ddH_2O$ successively. PCR amplification conditions are as follows: pre-heating at 94° C. for 5 min, 94° C. for 30 s, 60° C. for 30 s, 72° C. for 30 s, and then renaturation for 7 min after 35 cycles of amplification, to obtain a probe fragment.

Hybridization: 10.0 ml DIG Easy hyb is taken and added into a hybridization tube, then pre-hybridized for 2 h at 50° C. in a hybridizing furnace. The probe fragment is denatured in a PCR machine at 100° C. for 10 min, and immediately cooled in an ice-water bath for 5 min. Pre-hybridized solution is removed, newly denatured probe fragment is added into 10.0 ml DIG Easy hyb and mixed, hybridized overnight at 50° C. in a hybridization instrument.

Membrane washing and signal detection: After hybridization, a membrane is washed with 100 ml 1×SSC/0.1% SDS buffer for 2×5 min at room temperature, with 100 ml of 0.1×SSC/0.1% SDS for 2×15 min at 68° C. The membrane is balanced in 100 ml washing buffer for 2-5 min, sealed in 100 ml blocking solution for 1 h and then shaken it gently on a shaker. The membrane is reacted with 20 ml antibody solution for 30 min and meanwhile shaken it gently on the shaker. An antibody solution is removed and the membrane is washed with 100 ml washing buffer for 2×15 min. 1 ml of chemiluminescent substrate CSPDC ($18H_2OClNa_2O_7P$) of alkaline phosphatase dropwise on the front of the membrane (i.e. nucleic acid surface), and reaction is conducted in the absence of air at 15-25° C. for 5 min, then incubated at 37° C. for 10 min after excess liquid is removed. X-ray is used to expose, develop and fix in darkroom. The detection results are shown in FIGS. 4-12, where M is a DNA Marker, 37, 54 and 58 are different transgenic lines, CK is a non-transgenic control (i.e., wild-type plants control), and "+" is a positive control of the autotrophic nitrogenase expression vector pYP2082 for the plants.

It can be seen from the FIGS. 4-12 that the nine autotrophic nitrogen fixation genes are all expressed in plants. Northern blot fragments of genes hesA, nifb, nifH, nifD, nifK, nifN, nifE, nifV and nifX are all larger than their actual length of these genes, which are 760 bp, 1500 bp, 870 bp, 1450 bp, 1550 bp, 1300 bp, 1360 bp, 1150 bp, 400 bp respectively. It indicated that the obtained mRNA is a full-length fragment.

Example 6. Western Blot Analysis of Each Protein Expression in the Transgenic Plants Nine optimized autogenic nitrogen fixation genes are selected to express antigenic determinant in the nitrogenase-related Nif protein, and their coding nucleotide sequences are constructed into pET-28a-SUMO, prokaryotic expression immunogen, immune experimental Japanese white rabbits, after sacrificing the rabbits, an antibody is obtained after affinity purification. Plant tissue proteins are extracted, and performed SDS-PAGE electrophoresis with a constant voltage 120V of separation gel electrophoresis voltage. The membrane is transferred at a constant current of 200 mA for 60 min, here the membrane is a 0.45 μm nitrocellulose (NC) membrane. The membrane is sealed by TBST containing 3% (W/V) skimmed milk at room temperature for 1 h, incubated with a Nif protein diluted 1000 times by 3% (W/V) skimmed milk (TBST) overnight at 4° C., washed with TBST4 times, for 5 min each time, incubated with a horseradish peroxidase-conjugated goat anti-rabbit IgG antibody diluted 5000 times by 3% (W/V) skimmed milk (TBST) for 1 h at room temperature, washed with TBST 5 times, for 5 min each time, and colored via ECL. The detection results are shown in FIG. 13, where 37, 54, and 58 are different lines, CK is a control of non-transgenic plants.

Figure 13:
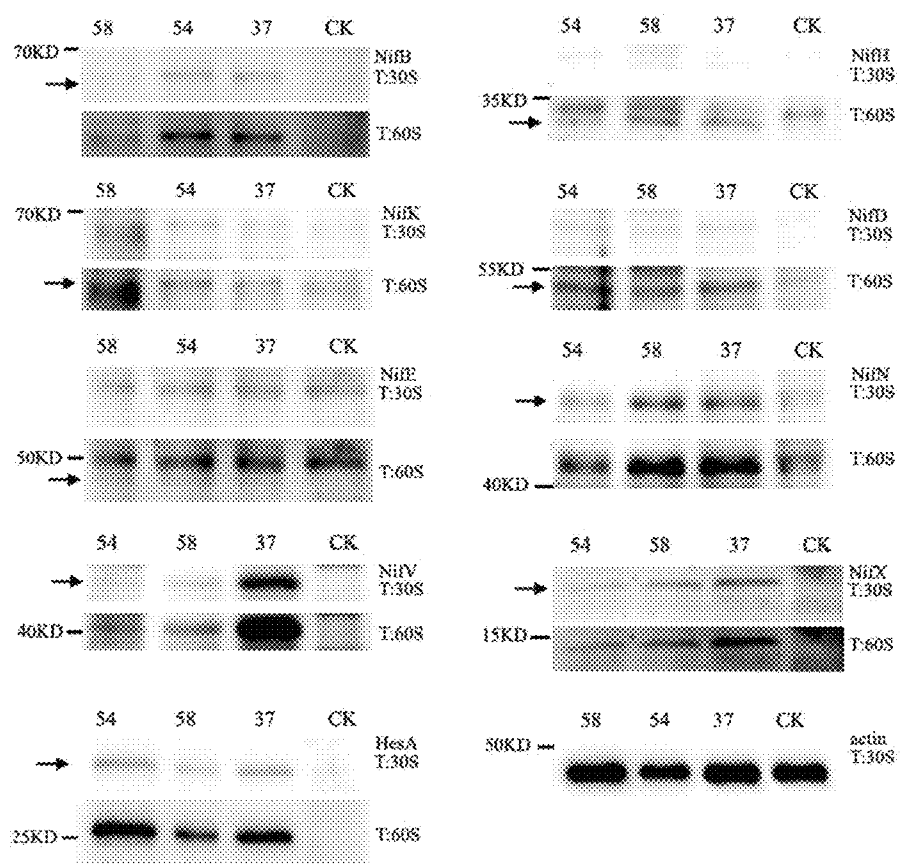
FIG. 13 shows Western detection results of the autotrophic nitrogen fixation genes in plants in example 6 of the present application.

It can be seen from FIG. 13 that the optimized nitrogen fixation genes hesA, nifB, nifH, nifD, nifK, nifN, nifE, nifV and nifX are expressed in the plant and detected their encoded proteins have a molecular weight of 28 kDa, 55 kDa, 31 kda, 54 kDa, 56 kda, 47 kDa, 50 kDa, 14 kda and 41 kda respectively, which are consistent with expectations. However, there are no relevant bands in the wild-type plants control, indicating that all the nitrogen fixation genes are successfully expressed in the plant.

Example 7 Screening of Low Nitrogen Culture Conditions for the Autotrophic Nitrogen Fixation Plants The nitrogenase expression cassette of the present application was transferred into plant to make transgenic autotrophic nitrogen fixation plant, seeds of the autotrophic nitrogen fixation plant are sterilized in vitro and grown on low-nitrogen ($KNO_3$ 10-100 mg/L) or nitrogen-free MS medium for cultivation, added 3.6-12.8 mg/L ferric citrate and 3-10 $Na_2MoO_4$. After growing for a period of time, fresh weight and chlorophyll content are measured respectively, here the non-transgenic plant is used as a control.

Figures 14, 15:
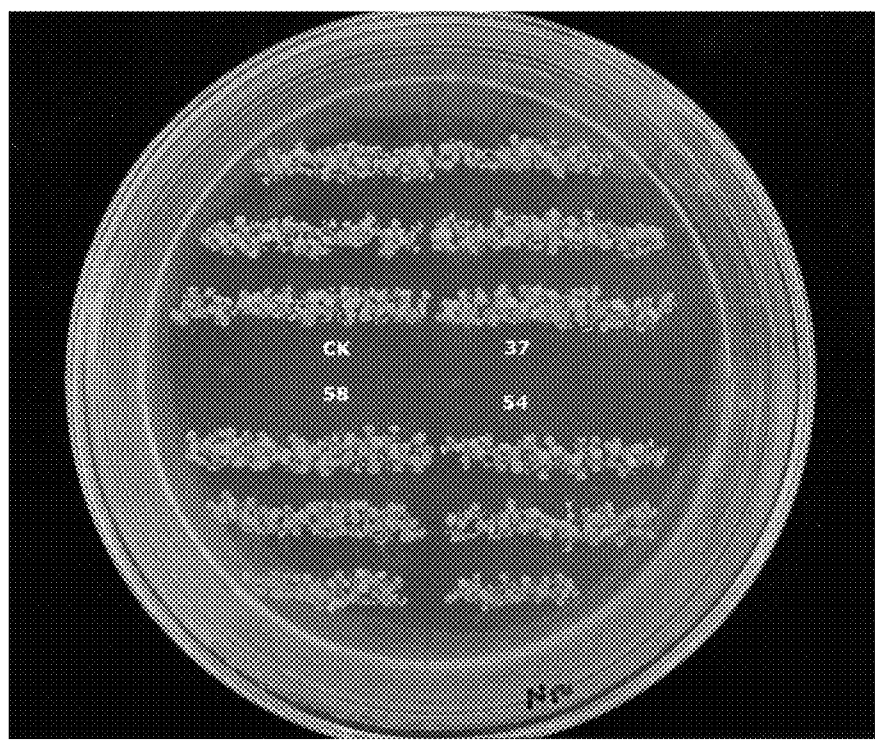
FIGS. 14-15 show phenotype of the plants in low nitrogen culture in example 7 of the present application.

The transgenic autotrophic nitrogen fixation rice lines are irrigated with the nitrogen-free MS medium and growth for 30 days, plant height and the fresh weight are 25-30% and 36-44% higher than the control. FIG. 14 shows their phenotypes, where 19 is the transgenic plant line and CK is the non-transgenic plant control.

The transgenic autotrophic nitrogen fixation *Arabidopsis* lines is cultured in low-nitrogen MS medium containing 50 mg/L $KNO_3$ for 15 days, fresh weight and chlorophyll content are 17-33% and 31-40% higher than the control plants respectively. FIG. 15 shows their phenotypes, where 37, 54 and 58 are different transgenic lines, and CK is the non-transgenic plant control.

It can be seen that for the transgenic autotrophic nitrogen fixation plants of the present application, their fresh weight and chlorophyll content are significantly higher than the non-transgenic plants under the low-nitrogen conditions.

Figures 16, 17:
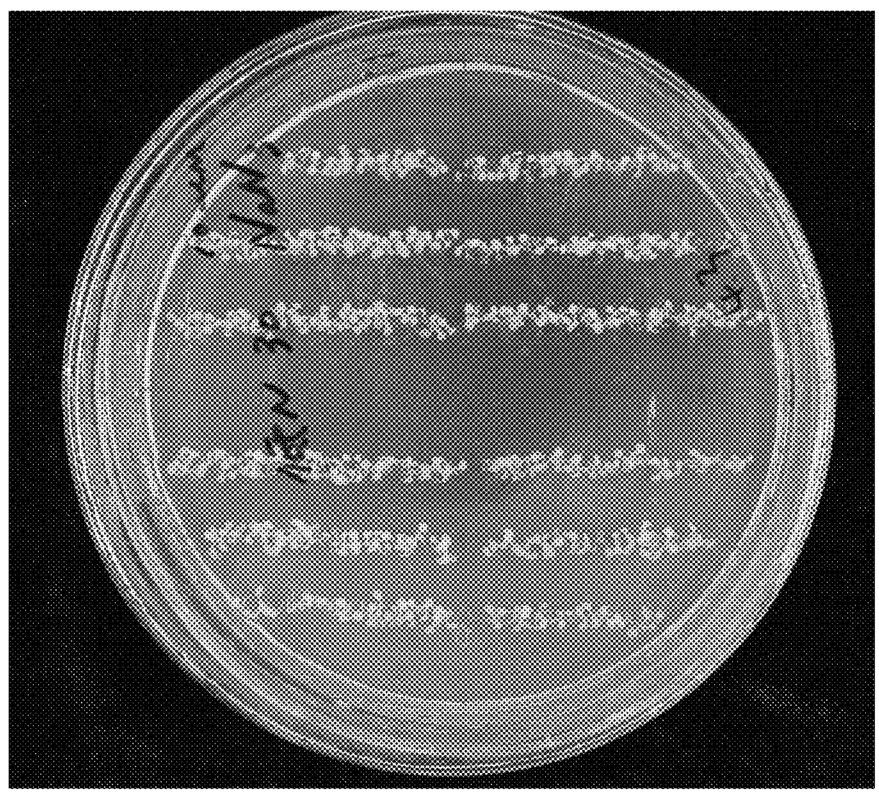
FIGS. 16-17 show KCN and $NaN_3$ resistant phenotypes of the autotrophic nitrogen fixation plants in example 8 of the present application.

Example 8 Resistant Culture Conditions of the Autotrophic Nitrogen Transgenic Plants Containing the Nitrogenase Expression Cassette The nitrogenase expression cassette of the present application was transferred into plant to make transgenic autotrophic nitrogen fixation plant. The seeds of the transgenic autotrophic nitrogen fixation plant are sterilized in vitro and grown on low-nitrogen ($KNO_3$ 10-100 mg/L) or nitrogen-free MS medium containing 0.1-0.2‰ KCN or 15 μM $NaN_3$, added 3.6-12.8 mg/L ferric citrate and 3-10 μM $Na_2MoO_4$. The non-transgenic plant is used as a control. After 30 days of growth, the fresh weight and chlorophyll content are measured respectively. FIGS. 16-17 show their resistance phenotypes, where FIG. 16 shows a resistance phenotype of the transgenic lines grown in the low-nitrogen medium (30 mg/L) containing 10 μM $NaN_3$ for 30 days, and FIG. 17 shows a resistance phenotype of the transgenic lines grown in the low-nitrogen medium (30 mg/L) containing 0.1‰ KCN for 30 days, where 37, 54 and 58 are different transgenic lines, and CK is non-transgenic plant control.

After the transgenic autogenic nitrogen fixation *Arabidopsis* lines are cultured in the low-nitrogen MS medium containing 0.1‰ KCN or 15 μM $NaN_3$ for 30 days, the fresh weight is 58% and 32% higher than those of the control, respectively. Therefore, for the autotrophic nitrogen transgenic plants containing the nitrogenase expression cassette, their fresh weight and chlorophyll content are significantly higher than the non-transgenic plants under the low-nitrogen conditions, indicating that they have obvious resistance to KCN or $NaN_3$.

Example 9 Determination of Nitrogenase Activity

For the autotrophic nitrogen transgenic plants containing the nitrogenase expression cassette of the present application, their proteins are extracted with plant extraction buffer containing Tris/HCl (0.1 M, pH 8.0), sodium dithionite (2 mM) and dithiothreitol (0.5 mM) and then centrifuged at 12,000 rpm for 15 min. Maintains anaerobic conditions during protein extraction, samples and the buffer are stored in a bag filled with argon ($Ar_2$), then all the samples and the buffers are washed out with $Ar_2$ to remove 02 from the solutions.

In vitro nitrogenase activities are tested by using an ATP-regeneration system with dithionite as the artificial electron donor. The test method refers to Willison and Vignais, Journal of General and Applied Microbiology. 1982, 128: 3001-3010.

Figure 18:
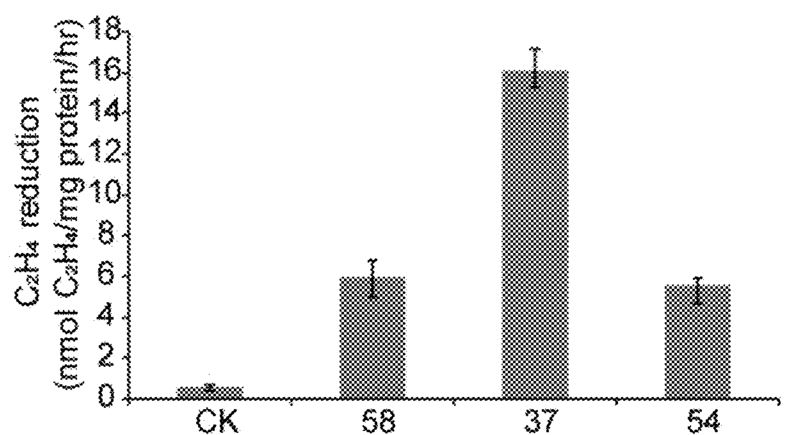
FIG. 18 shows detection results of nitrogenase activity of the autotrophic nitrogen fixation plants in vitro in example 9 of the present application.

0.2 ml of crude protein and 0.8 ml of enzyme reaction solution containing ATP, $MgCl_2$, creatine phosphate (Sigma), creatine phosphokinase (Sigma, 324 u/mg) and 40 mM MOPS-KOH (pH 7.4) are accurately placed in a serum bottle (10 ml), which was sealed with a rubber plug and rinsed twice with high-purity Ar, and Ar is injected to replace 10% volume of $C_2H_2$. The bottle is immediately placed at 30° C. and reacted for 1 h, the reaction was stopped with 30% TCA. Thereafter, 1 ml of gas is taken out of the rubber plug with a gas-tight syringe and injected into an Agilent 7890B gas chromatograph to quantify detect ethylene content. All treatments are repeated with three times, the in vitro detection results show that the transgenic plants have nitrogenase activity. As shown in FIG. 18, where 37, 54 and 58 are different lines respectively. It can be seen that, for the autotrophic nitrogen transgenic plants transferred into the nitrogenase expression cassette of the present application, the highest content of ethylene produced by reduction of acetylene can reach 16 nmol/mg protein/h, while the nitrogenase activity does not detected in the non-transgenic plants.

$^{15}N_2$ incorporation assay of the nitrogenase activity in vivo

Four-week-old *Arabidopsis* seedlings are transferred to a 50 ml flask containing 20 ml of solid nitrogen-deficient MS medium (i.e., containing 9 μM $Na_2MoO_4$ and 50 mM $Fe(III)C_6H_5O_7$) and grown for 3 days. Then, the flask is sealed with a rubber plug. Fifty percent of air in the flask is replaced with $^{15}N_2$ (99%+, Shanghai Engineering Research Centre for Stable Isotope). After 14 days of incubation at 25° C., the cultivated sample is dried at 60° C. and gradually ground into fine powder.

5 mg of the sample and 50 mg of copper oxide particles are put into a sample conversion tube, and then the air in the tube is extracted with a vacuum system. The sample conversion tube is sealed when its vacuum degree reaches 0.01 Pa. The sealed tube is heated in a muffle furnace at 530° C. for 4 h. After the reaction, the tube is cooled for mass spectrometry analysis.

The gas stream from the sample conversion tube is injected into ion source of a Finnigan MAT-271 mass spectrometer for isotope ratio measurement under conditions of high vacuum and low seepage rate. Each test contains 3 samples and is repeated 3 times. The isotope ratio of low ($^{15}N$=10.0%) and high abundance $^{15}N$ labeled semicarbazide ($^{15}N$>99.0%, Shanghai Research Institute of Chemical Industry) is used to detect internal precision of the mass spectrometer.

The isotopic composition of $^{15}N$ is determined by the isotope ratio of $^{15}N/^{14}N$. Due to low-level of $^{15}N$ content in the sample, the isotope ratios is represented by value of $\delta^{15}N$ ‰: $\delta^{15}N$ ‰$=[(^{15}N/^{14}N)_{sample}/(^{15}N/^{14}N)_{atmosphere}-1]\times1000$, where $(^{15}N/^{14}N)_{atmosphere}=0.366$ atom %.

Figure 19:
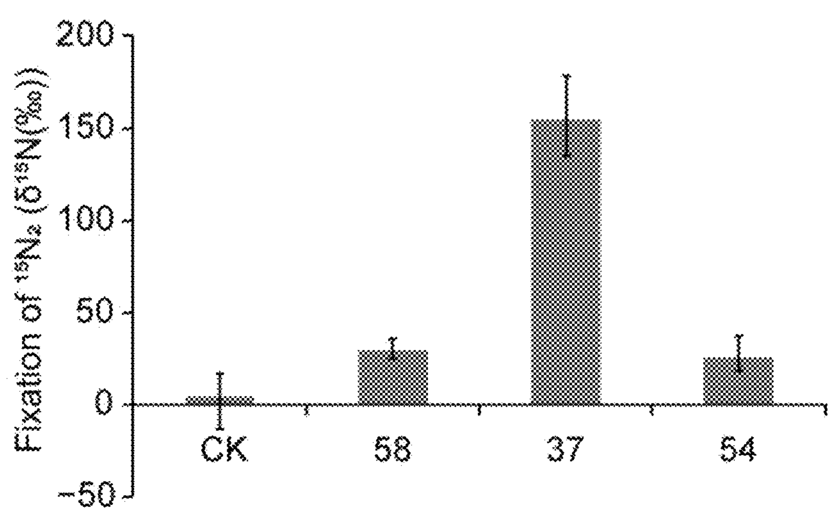
FIG. 19 shows detection results of nitrogenase activity of the autotrophic nitrogen fixation plants in vivo in example 9 of the present application.

The in vivo assay results show that the transgenic plants of the present application have nitrogenase activity, as shown in FIG. 19, where 37, 54 and 58 are different lines respectively. It can be seen that the content of $\delta^{15}N$ ‰ in the transgenic lines 37 can reach 154.9, while that of the non-transgenic control plant is only 4.6, the difference is very obvious.

What is claimed is:

1. Autotrophic nitrogen fixation genes for plants, comprising nitrogen fixation genes nifB, nifE, nifN, nifH, nifD, nifK, nifV, nifX, and hesA derived from nitrogen-fixing bacteria and optimized by plant expression patterns;

wherein nucleotide sequences of the nitrogen fixation genes nifB, nifE, nifN, nifH, nifD, nifK, nifV, nifX, and hesA optimized by the plant expression patterns are shown in SEQ ID No. 1, SEQ ID No. 2, SEQ ID No. 3, SEQ ID No. 4, SEQ ID No. 5, SEQ ID No. 6, SEQ ID No. 7, SEQ ID No. 8, and SEQ ID No. 9, respectively, and the nitrogen fixation genes optimized by the plant expression patterns are expressed in cytoplasm.

2. An autotrophic nitrogen fixation gene expression unit for plants, comprising one nitrogen fixation gene optimized by the plant expression patterns according to claim 1, a CaMV35SΩ promoter and a NOS terminator.

* * * * *

SEQUENCE LISTING

```
<160> NUMBER OF SEQ ID NOS: 305

<210> SEQ ID NO 1
<211> LENGTH: 1500
<212> TYPE: DNA
<213> ORGANISM: Artificial Sequence
```

<220> FEATURE:
<223> OTHER INFORMATION: Synthesized

<400> SEQUENCE: 1

```
atggactcac ttgctgatct ctccgaaact ccactggcac tggaaactct tcgtcgtcat     60
ccatgctaca acgaagaggc acatcgttac ttcgcacgta tccatcttcc tgttgcacct    120
gcttgcaaca tccagtgtca ctactgcaac cgtaagttcg actgtgtcaa cgagtcacgt    180
cctggtgtcg tctctgaact gctgactcct gaacaggctg catccaagac ctacggtgtt    240
gctgcacagc tgatgcagct gtctgttgtt ggtatcgctg gtcctggtga tccactggca    300
aacgctgagg caaccttcga caccttccgt cgtgttcgtg agactgtcaa ggatgtcatc    360
ttctgtctct caaccaacgg tctgactctg attcgtcaca tcgatcgtat cgtcgaactg    420
ggtatctcac acgtcaccat caccatcaac gctgtcgatc ctgttgttgg ttcacgtatc    480
tacggttggg tctatgatga aggtaaacgt tacgctggtg aggaggctgc acgtctgttg    540
atcgatcgtc agctggctgg tctgaagatg ctggcatcac gtggtgtctt gtgcaaggtc    600
aactctgtcc tgattcctga agtcaacgat gcacatcttc ctgaggttgc acgtgttgtc    660
aaggaacatg gtgctgttct gcacaacatc atgccactca tcattgcacc tggttcacgt    720
tacgaacagg aaggtatgcg tgcaccacgt ccacgtctgg ttcgtcagct tcaggaacaa    780
tgtgctgaag ctggtgctgt catcatgcgt cactgtcgtc agtgtcgtgc tgatgcaatc    840
ggtctgctgg gtgaggaccg taaccaggac ttcacttggg agaacattgc tgctgcacca    900
cctatggatg aagaggcacg tgcacagttc cagaaggaac tggatgagaa ggttcgtgtt    960
cgtatggaac gtaaggaggg tcagtctcac cacaagcaac catcaaccgg tgctggttgt   1020
tcttgtccac tgtctggtga caagcctgaa gcatccttca cctccaagcc tgtcttgatc   1080
gctgttgcat cacgtggtgg tggtaaggtc aaccagcact tcggtcgtgc aaaggagttc   1140
atgatctacg aatctgatgg tactatcgtc aacttcatcg gtatccgtaa ggtccagtcc   1200
tactgtcatg gtaaggctga ctgcaatggt gacaaggctg agaccatcaa ggagatcctg   1260
tcaatggttc atgactgtgc actgctgctg tcatccggta tcggtgaagc accaaaggag   1320
gcactccagg aagctggtgt cctgccaatc gtctgtggtg gtgacatcga ggagtctgtt   1380
ctggagtacg tcaagttcct gcgttacatg taccctgtcc agactggtaa gggttccaag   1440
cgtaacaagg gtgtcaaggg taatcactcc gacttgccta tcgaacactt cggtggttaa   1500
```

<210> SEQ ID NO 2
<211> LENGTH: 1362
<212> TYPE: DNA
<213> ORGANISM: Artificial Sequence
<220> FEATURE:
<223> OTHER INFORMATION: Synthesized

<400> SEQUENCE: 2

```
atggaaccag ctgtctccaa tggtcgtctt gaggtctcct gtggtaacaa gattcctaag     60
tctactccat gtccacgtcc tgttcctggt gaagcatctg gtggttgctc attcgatggt    120
gcacagatca ctctgattcc aatcgctgat gctgcacatc ttgttcatgg tccaatcgca    180
tgtcttggta actcttggga gtcacgtggt tcactgtcat ctggtcctga actctccgca    240
tacggtttca ctactgacct gggtgagcag gacatcatct tcggttctga acagaagctg    300
catgagtcaa tccgttacat cgtctcacgt ttcgcaccac ctgctgtctt cgtctacacc    360
acctgtgtca ctgcactcac tggtgaagac atcgaaggtg tctgcaaggc tgagtctgaa    420
```

```
cgtcttggta ctccaatcat ccctgtcaac tcacctggtt tcgttggttc caagaacctt    480

ggtactcgtc ttgctggtga tgtcctgttc cagcacatca tcggttcaac cgaacctgaa    540

cagaccacct cacatgacat caacctcatt ggtgagtaca acatcgctgg tgagatgtgg    600

cacattgaac gtctgatgca acaagcaggt atgtccatcc tgtcacgtat cactggtgat    660

ggtcgtttcc gtgaagttgg ttgggcacat cgtgcaaagg ctaacatggt tgtctgctca    720

cgtgcactgc tgggtctggc tgttcagatg gaacgtaagt acggtatccc atacttcgaa    780

ggttccttct acggtgcaaa ggagacctcc tactcattgc gtcagatggc atacctgact    840

ggtgatcgtg atgttgagcg tcgtgttgac aagctcgctg cacgtgagga gatgcgtctc    900

tcactggagc tggaaccata ccgtaagcag ctgaagggta agcgtgctgt cctctacact    960

ggtggtgtca agtcatggtc tgtcatcact gcactccagg agcttggtat caaggttgtt   1020

ggtgtcggta ctaacaagtc aactgctgag gatgtctcac gtatcgctga tcgtattggt   1080

gatgatgctg agtacattcc tgaaggtggt gcacgtcaga tcctcaagac tgttcgttca   1140

cgtaaggctg acatggtcat tgctggtggt cgtaacatgt acatggcact gaaggaacag   1200

attccattcg ttgacatcaa ccaagaacgt cacaaggcat acgctggtta cgatggtctg   1260

ttgtcacttg ccaaacagct tgtccatacc cttcagcatc ctgtctggga actgactgcc   1320

aaactggcac cttgggagga ggagactgag ttcgctgact aa                       1362
```

<210> SEQ ID NO 3
<211> LENGTH: 1308
<212> TYPE: DNA
<213> ORGANISM: Artificial Sequence
<220> FEATURE:
<223> OTHER INFORMATION: Synthesized

<400> SEQUENCE: 3

```
atgcttatca agtctgcaac caagcctgtc tctgtcaatc cactcaaggt tggtcagcct     60

cttggtggtg ttcttgcact tcagggtatg taccgttcaa tgccactgct gcatggtgca    120

cagggttgct ctgcattctc caaggcactg ctgactcgtc acttccgtga accaatcgct    180

gttcagacct ctgcactgca agagatggat gtcatcttcg acgctgatcg taacctggag    240

gaggcactgg atcacatctg gtccaagcat caccctgatg tcattggtgt catctctact    300

gcactcactg aggttgctgg tgtcgatttc cagtctcgtg tcaaggcatt caagcgtgag    360

cgtgcactga aggattctct gctgttctct gtctcacttc ctgacttcca tggttctctg    420

gagactggtt actcctctac cgtcgagtca ctcatggatg ctgttctcgg tttggcaggt    480

ggtaagtcac ctaagaagca acgtcgtact caggtcaacc tgcttcctgc atcctacctg    540

actgctggtg atgtcatgga gatcaaggac atcatcgcat cctttggtct ggaggtcatc    600

actcttcctg acatctccac ctccctgtct ggtcatctgc tgactggttt ctcaccactg    660

actcgtggtg gtactccact ggactctgca tgtcagatgc tggagtcatc ctgtactatc    720

gcaatcggtg catctatgga acgtcctgca cgtcgtctga ctcatgctgc tggtatccca    780

tatcacctgt tcgctggtct gtctggtctg gctgcatctg atgcattcat ccacttcctc    840

cagaaaatct cacgtgaacc tgcacctgtt cgtttccgtt ggcaacgtga gaacctgttg    900

gattctatgc tggatgcaca cttctactac tctggtgcat ctgctgtcgt tgcacttgaa    960

cctgatcaca tgctgtctac tgctgcatgg ctggaggaga tgggtgtcga actgaagcgt   1020

ctgatcactc catgctctac tcctgcactc cagaagactg aacgtgaagt ctggattggt   1080

gatctggatg atgctgagga gtctgcacag ggtgttgatc tgtggatctc caactcacat   1140
```

```
ggtcgtaagg gtgctgcacg tgctggtgca tcattcgttc ctgctggtct gcctgtctat   1200

gatgaacttg gtgcacacac ttctgtctct gttggttatc gtggtactat ggaatgggtc   1260

aacaaggttg gtaacgtctt gctcgctgaa cgtggtcgtg gtggttaa                1308
```

<210> SEQ ID NO 4
<211> LENGTH: 867
<212> TYPE: DNA
<213> ORGANISM: Artificial Sequence
<220> FEATURE:
<223> OTHER INFORMATION: Synthesized

<400> SEQUENCE: 4

```
atgcgtcaga ttgcattcta cggtaagggt ggtatcggta agtctactac ctcacagaac     60

acccttgcac aacttgcaac caagttcaag cagaagatca tgatcgttgg ttgcgaccca    120

aaggctgact ccactcgtct gatcctgaac accaaggcac aacagactgt cctgcacctg    180

gctgctgaac gtggtactgt tgaggatctg gaactggagg atgttgttca gaagggtttc    240

ggtgacatcc tgaacgttga gtgtggtggt cctgaacctg gtgttggttg tgctggtcgt    300

ggtatcatca ctgcaatcaa cttcctggag gaagagggtg catacgaagg tctggacttc    360

gtctcctacg atgtcctggg tgatgtcgtt tgtggtggtt tcgcaatgcc tatccgtgag    420

aagaaggcac aggaaatcta catcgtctgc tctggtgaga tgatggcaat gtatgctgcc    480

aacaacattg cacgtggtat cctgaagtac gcaaactctg gtggtgttcg tttgggtggt    540

ttgatctgca attctcgtaa caccgatctg gaagctgaac tgatcaccga acttgcacgt    600

cgtctgaaca cccagatgat ccacttcctg ccacgtgaca acgttgtcca acatgctgaa    660

ctgcgtcgta tgactgtcac tcagtacaat cctgaacaca agcaggctgc tgagtatgag    720

gagctggctg gtaagatcct gaacaacgac atgctgaccg ttcctactcc tatctcaatg    780

gaagaccttg aggatctgtt gatggagttc ggtatcatcg aggacgaaga gactgccatc    840

aacaaggctg aggcatctgg tcagtaa                                        867
```

<210> SEQ ID NO 5
<211> LENGTH: 1449
<212> TYPE: DNA
<213> ORGANISM: Artificial Sequence
<220> FEATURE:
<223> OTHER INFORMATION: Synthesized

<400> SEQUENCE: 5

```
atgtcatcaa tcgttgacaa gggtaagcag attgttgagg agattcttga ggtctatcca     60

aagaaggcaa agaaggatcg taccaagcac ttcgagattg ctgatgagga acttgtcaac    120

tgtggtactt gctccatcaa gtccaacatg aagtcacgtc ctggtgtcat gactgcacgt    180

ggttgtgcat acgctggttc caagggtgtt gtctggggtc ctatcaagga tatggttcac    240

atctcacatg gtccaatcgg ttgtggtcag tactcatggg gtactcgtcg taactacgct    300

aacggtatct tgggtatcga caacttcact gcaatgcaga tcacctccaa cttccaggaa    360

aaggacatcg tcttcggtgg tgacaagaag ctggaggtca tctgtcgtga gatcaaggag    420

atgttcccac tggctaaggg tatctctgtc cagtctgagt gtcctgttgg tctgatcggt    480

gatgacattg gtgctgttgc caagaagatg actgaggaac ttggtatccc tgtcatccct    540

gttcgttgtg aaggtttccg tggtgtctct cagtcacttg gtcatcacat cgcaaacgac    600

gcaatccgtg acttcctcat gggtcgtcgt gaactgaagg agtgtggtcc atacgatgtc    660
```

-continued

```
tccatcattg gtgactacaa cattggtggt gatgcatggg catctcgtat cttgcttgag    720

gagatgggtc ttcgtgtcat tgcacagtgg tctggtgatg gtactatcaa cgaacttggt    780

atcgcacaca agtccaagct gaacctgatc cactgtcacc gttccatgaa ctacatgtgc    840

accactatgg aacaggagta tggtattcct tggatggagt acaacttctt cggtccaacc    900

aagactatgg agtcacttcg tgcaatcgct gcacgtttcg atgagactat ccaggagaag    960

tgtgaacagg tcattgcaca gtacatgcca cagatggaag cagtcatccg taagtaccgt   1020

ccacgtctgg aaggtaagaa ggtcatgctt ctgattggtg gtctgcgtgc acgtcacact   1080

atcggtgcat acgaggatct gggtatggag attgttgcta ctggttacga gttcgcacac   1140

aaggacgact acgagaagac cttccctgat gtcaaggagg gtactatcct gtacgatgat   1200

ccaactgcat acgaactgga ggaacttgca caacgtctga acatcgactt gatgggtgct   1260

ggtgtcaagg agaagtacgt ctaccacaag atgggtattc cattccgtca gatgcactcc   1320

tgggactact ctggtcctta ccatggtttc gacggtttca aaatcttcgc acgtgacatg   1380

gatatgacca tcaactcacc tgtttggtct ctgcttccat cacgtcagac tgctgaggtt   1440

cctgtctaa                                                           1449


<210> SEQ ID NO 6
<211> LENGTH: 1530
<212> TYPE: DNA
<213> ORGANISM: Artificial Sequence
<220> FEATURE:
<223> OTHER INFORMATION: Synthesized

<400> SEQUENCE: 6

atgtctgaac gtcctaacat tgttgatcac aaccaactgt tccgtcagga caagtacgtt     60

cgtcaacgtg aagagaagcg tgcattcgag gcaccatgtt cacctgagga ggtcactgat    120

actctggagt acaccaagac caaggagtac aaggacaaga acttcgcacg tactgctgtt    180

gtcgtcaacc ctgcaaaggc atgtcaacca ctgggtgctg tcatggctgc actgggtttc    240

gagaagaccc ttccattcat ccatggttca cagggttgca ctgcatactt ccgttctcac    300

cttgcacgtc acttcaagga acctgtccct gctgtctcca cctccatgac tgaggacgct    360

gctgtcttcg gtggtatgcg taacctcatc gatggtatcg agaactgcat tgcactgtat    420

caacctgaga tgattgctgt ctgcaccacc tgtatggctg aggtcattgg tgatgatctg    480

tctgcattcc ttgccaacgc acgtcaggag ggtgtccttc ctgaggacat gcctgttcca    540

ttcgcaaaca ctccatcctt ctctggttca cacatcactg gttacgatgc aatgctgcgt    600

tctgttctgg aaaccctgta caacaagtct ggtcgtactg cacaacctgg tcatgaactg    660

aagctgaacg tcctgcttgg tttcgatggt tacactggta acttcgctga gatgcgtcgt    720

atgcttggta tgttcggtgc tacctacacc atccttggtg atcattcctc caacttcgac    780

tctggtgcaa ctggtgagta ctcctactac tatggtggta ctccacttga ggatgttcct    840

aaggctgctg atgctgctgg tactctggca atccagcagt actcacttcg taagactctt    900

ggttacatga agcaaacttg ggtcagcag gtctcatcca tctccactcc actgggtatc     960

cgtgctactg atcgtctgct tgaggaaatc tcacgtctgt ctggtcgtga gatccctgag   1020

gcactgaagc aggaacgtgc acgtatcgtc gatgcaatga tggactcaca tgcatacctg   1080

catggtaagc gtgttgctat ggctggtgat cctgacatgc tcattggtct gatcggtttc   1140

tgtctggaac tgggtatgga acctgtccac attgtctgct ccaacggtga tcgtaagttc   1200

gagaaggaag ctgagcttct tctgaagtcc tcaccatacg gtgctgaagc aaccgttcac   1260
```

```
tctggtcagg atctgtggca catgcgttct ctgctgttcc aggaccctgt tgatctggca   1320

atcggttcat cacatctgaa gttcgctgcc aaggaggctg agatccctct gcttcgtgtt   1380

ggtttcccaa tcttcgatcg tcatcacctg catcgttacc caatcattgg ttatcagggt   1440

gcactgaacc tgctcactca gttcgtcaac accatcctcg acgttatgga ggaacaggca   1500

cctgatcact ccttcgacct ggttcgttaa                                     1530
```

<210> SEQ ID NO 7
<211> LENGTH: 1137
<212> TYPE: DNA
<213> ORGANISM: Artificial Sequence
<220> FEATURE:
<223> OTHER INFORMATION: Synthesized

<400> SEQUENCE: 7

```
atgtctcgtc tgcacatctg tgatactaca cttcgtgatg gtgaacaggc acctggtgtt     60

gcattctctg ctgaggagaa gaccgagatt gcaatcatgc tggattctgc tggtgtcgag    120

caggctgaga tcggtattcc tgcaatgggt aagactgagt gccgttccat tgcacgtatc    180

gctgcactcg gtcttcagat gaagctcatg acttggaacc gtgctgtctt caccgacatc    240

gatgcaaccg aatccactgg tgttggttgg gcacacatct ctgtccctgt ctcaactgtc    300

cagatgaagt ctaagctggg tatgaaccct gaacaggtca ctgaactgat ccgtaagtcc    360

gttgactatg cactgtgcaa gggtctgact gtctctgttg gtttcgagga tgcatcacgt    420

gcagatgatc tgttccttga gcagttggca aaccagctct atcgtgatgg tatccgtcgt    480

ttccgttacg ctgatactct gtctgttcat caccctgctg caatcgctgc acgtatcgat    540

cgtcttgtct cacgtgttcc acaggacgtc gaactggaga tccactgtca caacgactac    600

ggtctggcac ttgccaacac tctggctgca ctgcaagctg gtgctgtttg ggcatcaacc    660

actgtctctg gtcttggtga acgtgctggt aacactgcac tggaggaggt tgtcatgtct    720

tggcgtgatc tgtaccaagg tacttgctct gtccgtcctg aactgctgaa tccactggct    780

gcactggtct ccaaggcatc caaccgtatc atccctgaag gtaagccaat cgttggtgac    840

atggtcttcg cacatgaatc tggtatccac atcaatggtc tgctgaagga acgtgctgca    900

taccaggcac ttgacccaac tgaactgggt actgaccact cattcgtcct tggtaagcac    960

tctggtcgtt ctgctgtcca gtacatgctg gaacaggaag gtatcgaggc tggctctggt   1020

gagatcaagt tcctgcttga acgtcttcgt ctggttggtg aagaccctaa gcgtgtcatc   1080

cattctgctg acttgcgtcg ttggctccag tactaccctg ctgaactgcc taagtaa      1137
```

<210> SEQ ID NO 8
<211> LENGTH: 390
<212> TYPE: DNA
<213> ORGANISM: Artificial Sequence
<220> FEATURE:
<223> OTHER INFORMATION: Synthesized

<400> SEQUENCE: 8

```
atgaaggttg cattcgcaac tgaagatggt gtccttgtca atgcacactt cggtcagtca     60

ccaatgttca ccatcttcga gattcgtcac tctggtgtcc agttcctgga acatcgtcgt    120

atcgcactgg gttctgacga gaacgaggct ggtaagattg cctcacgtat cggtctgatc    180

gaggactgtg cactgatctt cctggttcag atcggtgcat ctgctgctgc acaggtcact    240

aagcgtacca tcatgcctgt caaggtcgca ttcggttcta ccatcgagga acaggttcag    300
```

cgtcttcaga acatgctgac tcgtaaccca ccaatgtggc ttgcaaagat cctgcacgct 360
gaggagggtt ctggtaaggc tgagtcataa 390

<210> SEQ ID NO 9
<211> LENGTH: 765
<212> TYPE: DNA
<213> ORGANISM: Artificial Sequence
<220> FEATURE:
<223> OTHER INFORMATION: Synthesized

<400> SEQUENCE: 9
atggttcaac ttcttgaaga ttcacgttat ggtcgtcagt tgaagctgct tggtgttgaa 60
ggtcagaatc gtctgaagca ggcaaccgtt atggttgctg gtatcggtgg tctgggtggt 120
gctgctgcaa tgtatcttgc tgctgctggt gttggtaagc tgatcttggc acatgagggt 180
gtcattcatc ttcctgatat gaatcgtcag gttctgatgg attctggtcg tatcggtgag 240
gaacgtatgg agactgcact gcaacatctg catcgtatca accctgagac tgaacttgaa 300
ggtcatgcac atcgtatcac tgaagagtca tctggtcctt gggttgaagc atctgacatc 360
gtcattgatg cacgttacga cttccctgaa cgttacgcac tgaatcgtct gtgtgttcgt 420
catggtcgtc caatgattga agctgccatg tatgcatacg aagtctcact gatgactatc 480
gaccctggta agactgcttg ccttgagtgt ctgtatcctg aaggtggtca gccttgggaa 540
ccactgggtt tccctgtcct gggtgcaacc tctggtctga ttggttgcat ggctgcactg 600
gaagctgtca agtggatcac tgatgctggt aatctgttca ctgatcgtat gtaccgtatg 660
aacgttctgg acatgtcatc atgcactatc gctgtcaagc gtaacccacg ttgtccatgc 720
tgtggtactg gtggtgacac tgatgagtct gttgcatacc tgtaa 765

<210> SEQ ID NO 10
<211> LENGTH: 60
<212> TYPE: DNA
<213> ORGANISM: Artificial Sequence
<220> FEATURE:
<223> OTHER INFORMATION: Synthesized

<400> SEQUENCE: 10
atgcgtcaga ttgcattcta cggtaagggt ggtatcggta agtctactac ctcacagaac 60

<210> SEQ ID NO 11
<211> LENGTH: 60
<212> TYPE: DNA
<213> ORGANISM: Artificial Sequence
<220> FEATURE:
<223> OTHER INFORMATION: Synthesized

<400> SEQUENCE: 11
tgatcttctg cttgaacttg gttgcaagtt gtgcaagggt gttctgtgag gtagtagact 60

<210> SEQ ID NO 12
<211> LENGTH: 60
<212> TYPE: DNA
<213> ORGANISM: Artificial Sequence
<220> FEATURE:
<223> OTHER INFORMATION: Synthesized

<400> SEQUENCE: 12
caagttcaag cagaagatca tgatcgttgg ttgcgaccca aaggctgact ccactcgtct 60

<210> SEQ ID NO 13
<211> LENGTH: 60

<212> TYPE: DNA
<213> ORGANISM: Artificial Sequence
<220> FEATURE:
<223> OTHER INFORMATION: Synthesized

<400> SEQUENCE: 13
caggtgcagg acagtctgtt gtgccttggt gttcaggatc agacgagtgg agtcagcctt 60

<210> SEQ ID NO 14
<211> LENGTH: 60
<212> TYPE: DNA
<213> ORGANISM: Artificial Sequence
<220> FEATURE:
<223> OTHER INFORMATION: Synthesized

<400> SEQUENCE: 14
aacagactgt cctgcacctg gctgctgaac gtggtactgt tgaggatctg gaactggagg 60

<210> SEQ ID NO 15
<211> LENGTH: 60
<212> TYPE: DNA
<213> ORGANISM: Artificial Sequence
<220> FEATURE:
<223> OTHER INFORMATION: Synthesized

<400> SEQUENCE: 15
tcaacgttca ggatgtcacc gaaacccttc tgaacaacat cctccagttc cagatcctca 60

<210> SEQ ID NO 16
<211> LENGTH: 60
<212> TYPE: DNA
<213> ORGANISM: Artificial Sequence
<220> FEATURE:
<223> OTHER INFORMATION: Synthesized

<400> SEQUENCE: 16
ggtgacatcc tgaacgttga gtgtggtggt cctgaacctg gtgttggttg tgctggtcgt 60

<210> SEQ ID NO 17
<211> LENGTH: 60
<212> TYPE: DNA
<213> ORGANISM: Artificial Sequence
<220> FEATURE:
<223> OTHER INFORMATION: Synthesized

<400> SEQUENCE: 17
caccctcttc ctccaggaag ttgattgcag tgatgatacc acgaccagca caaccaacac 60

<210> SEQ ID NO 18
<211> LENGTH: 60
<212> TYPE: DNA
<213> ORGANISM: Artificial Sequence
<220> FEATURE:
<223> OTHER INFORMATION: Synthesized

<400> SEQUENCE: 18
cttcctggag gaagagggtg catacgaagg tctggacttc gtctcctacg atgtcctggg 60

<210> SEQ ID NO 19
<211> LENGTH: 60
<212> TYPE: DNA
<213> ORGANISM: Artificial Sequence
<220> FEATURE:
<223> OTHER INFORMATION: Synthesized

<400> SEQUENCE: 19
ctcacggata ggcattgcga aaccaccaca aacgacatca cccaggacat cgtaggagac 60

<210> SEQ ID NO 20
<211> LENGTH: 60
<212> TYPE: DNA
<213> ORGANISM: Artificial Sequence
<220> FEATURE:
<223> OTHER INFORMATION: Synthesized

<400> SEQUENCE: 20
tcgcaatgcc tatccgtgag aagaaggcac aggaaatcta catcgtctgc tctggtgaga 60

<210> SEQ ID NO 21
<211> LENGTH: 60
<212> TYPE: DNA
<213> ORGANISM: Artificial Sequence
<220> FEATURE:
<223> OTHER INFORMATION: Synthesized

<400> SEQUENCE: 21
ataccacgtg caatgttgtt ggcagcatac attgccatca tctcaccaga gcagacgatg 60

<210> SEQ ID NO 22
<211> LENGTH: 60
<212> TYPE: DNA
<213> ORGANISM: Artificial Sequence
<220> FEATURE:
<223> OTHER INFORMATION: Synthesized

<400> SEQUENCE: 22
aacaacattg cacgtggtat cctgaagtac gcaaactctg gtggtgttcg tttgggtggt 60

<210> SEQ ID NO 23
<211> LENGTH: 60
<212> TYPE: DNA
<213> ORGANISM: Artificial Sequence
<220> FEATURE:
<223> OTHER INFORMATION: Synthesized

<400> SEQUENCE: 23
gttcagcttc cagatcggtg ttacgagaat tgcagatcaa accacccaaa cgaacaccac 60

<210> SEQ ID NO 24
<211> LENGTH: 60
<212> TYPE: DNA
<213> ORGANISM: Artificial Sequence
<220> FEATURE:
<223> OTHER INFORMATION: Synthesized

<400> SEQUENCE: 24
caccgatctg gaagctgaac tgatcaccga acttgcacgt cgtctgaaca cccagatgat 60

<210> SEQ ID NO 25
<211> LENGTH: 60
<212> TYPE: DNA
<213> ORGANISM: Artificial Sequence
<220> FEATURE:
<223> OTHER INFORMATION: Synthesized

<400> SEQUENCE: 25
ttcagcatgt tggacaacgt tgtcacgtgg caggaagtgg atcatctggg tgttcagacg 60

<210> SEQ ID NO 26
<211> LENGTH: 60
<212> TYPE: DNA
<213> ORGANISM: Artificial Sequence
<220> FEATURE:
<223> OTHER INFORMATION: Synthesized

<400> SEQUENCE: 26
acgttgtcca acatgctgaa ctgcgtcgta tgactgtcac tcagtacaat cctgaacaca 60

<210> SEQ ID NO 27
<211> LENGTH: 60
<212> TYPE: DNA
<213> ORGANISM: Artificial Sequence
<220> FEATURE:
<223> OTHER INFORMATION: Synthesized

<400> SEQUENCE: 27
aggatcttac cagccagctc ctcatactca gcagcctgct tgtgttcagg attgtactga 60

<210> SEQ ID NO 28
<211> LENGTH: 60
<212> TYPE: DNA
<213> ORGANISM: Artificial Sequence
<220> FEATURE:
<223> OTHER INFORMATION: Synthesized

<400> SEQUENCE: 28
gagctggctg gtaagatcct gaacaacgac atgctgaccg ttcctactcc tatctcaatg 60

<210> SEQ ID NO 29
<211> LENGTH: 60
<212> TYPE: DNA
<213> ORGANISM: Artificial Sequence
<220> FEATURE:
<223> OTHER INFORMATION: Synthesized

<400> SEQUENCE: 29
cgatgatacc gaactccatc aacagatcct caaggtcttc cattgagata ggagtaggaa 60

<210> SEQ ID NO 30
<211> LENGTH: 60
<212> TYPE: DNA
<213> ORGANISM: Artificial Sequence
<220> FEATURE:
<223> OTHER INFORMATION: Synthesized

<400> SEQUENCE: 30
gatggagttc ggtatcatcg aggacgaaga gactgccatc aacaaggctg aggcatctgg 60

<210> SEQ ID NO 31
<211> LENGTH: 27
<212> TYPE: DNA
<213> ORGANISM: Artificial Sequence
<220> FEATURE:
<223> OTHER INFORMATION: Synthesized

<400> SEQUENCE: 31
ttactgacca gatgcctcag ccttgtt 27

<210> SEQ ID NO 32
<211> LENGTH: 60
<212> TYPE: DNA
<213> ORGANISM: Artificial Sequence
<220> FEATURE:
<223> OTHER INFORMATION: Synthesized

<400> SEQUENCE: 32
atgtcatcaa tcgttgacaa gggtaagcag attgttgagg agattcttga ggtctatcca 60

<210> SEQ ID NO 33
<211> LENGTH: 60
<212> TYPE: DNA
<213> ORGANISM: Artificial Sequence
<220> FEATURE:
<223> OTHER INFORMATION: Synthesized

<400> SEQUENCE: 33
caatctcgaa gtgcttggta cgatccttct ttgccttctt tggatagacc tcaagaatct 60

<210> SEQ ID NO 34
<211> LENGTH: 60
<212> TYPE: DNA
<213> ORGANISM: Artificial Sequence
<220> FEATURE:
<223> OTHER INFORMATION: Synthesized

<400> SEQUENCE: 34
taccaagcac ttcgagattg ctgatgagga acttgtcaac tgtggtactt gctccatcaa 60

<210> SEQ ID NO 35
<211> LENGTH: 60
<212> TYPE: DNA
<213> ORGANISM: Artificial Sequence
<220> FEATURE:
<223> OTHER INFORMATION: Synthesized

<400> SEQUENCE: 35
acgtgcagtc atgacaccag gacgtgactt catgttggac ttgatggagc aagtaccaca 60

<210> SEQ ID NO 36
<211> LENGTH: 60
<212> TYPE: DNA
<213> ORGANISM: Artificial Sequence
<220> FEATURE:
<223> OTHER INFORMATION: Synthesized

<400> SEQUENCE: 36
ctggtgtcat gactgcacgt ggttgtgcat acgctggttc caagggtgtt gtctggggtc 60

<210> SEQ ID NO 37
<211> LENGTH: 60
<212> TYPE: DNA
<213> ORGANISM: Artificial Sequence
<220> FEATURE:
<223> OTHER INFORMATION: Synthesized

<400> SEQUENCE: 37
ccgattggac catgtgagat gtgaaccata tccttgatag gaccccagac aacacccttg 60

<210> SEQ ID NO 38
<211> LENGTH: 60
<212> TYPE: DNA
<213> ORGANISM: Artificial Sequence
<220> FEATURE:
<223> OTHER INFORMATION: Synthesized

<400> SEQUENCE: 38
atctcacatg gtccaatcgg ttgtggtcag tactcatggg gtactcgtcg taactacgct 60

<210> SEQ ID NO 39
<211> LENGTH: 60
<212> TYPE: DNA
<213> ORGANISM: Artificial Sequence
<220> FEATURE:
<223> OTHER INFORMATION: Synthesized

<400> SEQUENCE: 39
tctgcattgc agtgaagttg tcgataccca agataccgtt agcgtagtta cgacgagtac 60

<210> SEQ ID NO 40
<211> LENGTH: 60
<212> TYPE: DNA
<213> ORGANISM: Artificial Sequence
<220> FEATURE:
<223> OTHER INFORMATION: Synthesized

<400> SEQUENCE: 40
caacttcact gcaatgcaga tcacctccaa cttccaggaa aaggacatcg tcttcggtgg 60

<210> SEQ ID NO 41
<211> LENGTH: 60
<212> TYPE: DNA
<213> ORGANISM: Artificial Sequence
<220> FEATURE:
<223> OTHER INFORMATION: Synthesized

<400> SEQUENCE: 41
ctccttgatc tcacgacaga tgacctccag cttcttgtca ccaccgaaga cgatgtcctt 60

<210> SEQ ID NO 42
<211> LENGTH: 60
<212> TYPE: DNA
<213> ORGANISM: Artificial Sequence
<220> FEATURE:
<223> OTHER INFORMATION: Synthesized

<400> SEQUENCE: 42
tctgtcgtga gatcaaggag atgttcccac tggctaaggg tatctctgtc cagtctgagt 60

<210> SEQ ID NO 43
<211> LENGTH: 60
<212> TYPE: DNA
<213> ORGANISM: Artificial Sequence
<220> FEATURE:
<223> OTHER INFORMATION: Synthesized

<400> SEQUENCE: 43
gcaacagcac caatgtcatc accgatcaga ccaacaggac actcagactg gacagagata 60

<210> SEQ ID NO 44
<211> LENGTH: 60
<212> TYPE: DNA
<213> ORGANISM: Artificial Sequence
<220> FEATURE:
<223> OTHER INFORMATION: Synthesized

<400> SEQUENCE: 44
gatgacattg gtgctgttgc caagaagatg actgaggaac ttggtatccc tgtcatccct 60

<210> SEQ ID NO 45
<211> LENGTH: 60
<212> TYPE: DNA
<213> ORGANISM: Artificial Sequence
<220> FEATURE:
<223> OTHER INFORMATION: Synthesized

<400> SEQUENCE: 45
caagtgactg agagacacca cggaaacctt cacaacgaac agggatgaca gggataccaa 60

<210> SEQ ID NO 46

<211> LENGTH: 60
<212> TYPE: DNA
<213> ORGANISM: Artificial Sequence
<220> FEATURE:
<223> OTHER INFORMATION: Synthesized

<400> SEQUENCE: 46
tggtgtctct cagtcacttg gtcatcacat cgcaaacgac gcaatccgtg acttcctcat 60

<210> SEQ ID NO 47
<211> LENGTH: 60
<212> TYPE: DNA
<213> ORGANISM: Artificial Sequence
<220> FEATURE:
<223> OTHER INFORMATION: Synthesized

<400> SEQUENCE: 47
gacatcgtat ggaccacact ccttcagttc acgacgaccc atgaggaagt cacggattgc 60

<210> SEQ ID NO 48
<211> LENGTH: 60
<212> TYPE: DNA
<213> ORGANISM: Artificial Sequence
<220> FEATURE:
<223> OTHER INFORMATION: Synthesized

<400> SEQUENCE: 48
agtgtggtcc atacgatgtc tccatcattg gtgactacaa cattggtggt gatgcatggg 60

<210> SEQ ID NO 49
<211> LENGTH: 60
<212> TYPE: DNA
<213> ORGANISM: Artificial Sequence
<220> FEATURE:
<223> OTHER INFORMATION: Synthesized

<400> SEQUENCE: 49
atgacacgaa gacccatctc ctcaagcaag atacgagatg cccatgcatc accaccaatg 60

<210> SEQ ID NO 50
<211> LENGTH: 60
<212> TYPE: DNA
<213> ORGANISM: Artificial Sequence
<220> FEATURE:
<223> OTHER INFORMATION: Synthesized

<400> SEQUENCE: 50
gagatgggtc ttcgtgtcat tgcacagtgg tctggtgatg gtactatcaa cgaacttggt 60

<210> SEQ ID NO 51
<211> LENGTH: 60
<212> TYPE: DNA
<213> ORGANISM: Artificial Sequence
<220> FEATURE:
<223> OTHER INFORMATION: Synthesized

<400> SEQUENCE: 51
ggtgacagtg gatcaggttc agcttggact tgtgtgcgat accaagttcg ttgatagtac 60

<210> SEQ ID NO 52
<211> LENGTH: 60
<212> TYPE: DNA
<213> ORGANISM: Artificial Sequence
<220> FEATURE:
<223> OTHER INFORMATION: Synthesized

<400> SEQUENCE: 52
gaacctgatc cactgtcacc gttccatgaa ctacatgtgc accactatgg aacaggagta 60

<210> SEQ ID NO 53
<211> LENGTH: 60
<212> TYPE: DNA
<213> ORGANISM: Artificial Sequence
<220> FEATURE:
<223> OTHER INFORMATION: Synthesized

<400> SEQUENCE: 53
ggttggaccg aagaagttgt actccatcca aggaatacca tactcctgtt ccatagtggt 60

<210> SEQ ID NO 54
<211> LENGTH: 60
<212> TYPE: DNA
<213> ORGANISM: Artificial Sequence
<220> FEATURE:
<223> OTHER INFORMATION: Synthesized

<400> SEQUENCE: 54
acaacttctt cggtccaacc aagactatgg agtcacttcg tgcaatcgct gcacgtttcg 60

<210> SEQ ID NO 55
<211> LENGTH: 60
<212> TYPE: DNA
<213> ORGANISM: Artificial Sequence
<220> FEATURE:
<223> OTHER INFORMATION: Synthesized

<400> SEQUENCE: 55
tgtgcaatga cctgttcaca cttctcctgg atagtctcat cgaaacgtgc agcgattgca 60

<210> SEQ ID NO 56
<211> LENGTH: 60
<212> TYPE: DNA
<213> ORGANISM: Artificial Sequence
<220> FEATURE:
<223> OTHER INFORMATION: Synthesized

<400> SEQUENCE: 56
tgtgaacagg tcattgcaca gtacatgcca cagatggaag cagtcatccg taagtaccgt 60

<210> SEQ ID NO 57
<211> LENGTH: 60
<212> TYPE: DNA
<213> ORGANISM: Artificial Sequence
<220> FEATURE:
<223> OTHER INFORMATION: Synthesized

<400> SEQUENCE: 57
caccaatcag aagcatgacc ttcttacctt ccagacgtgg acggtactta cggatgactg 60

<210> SEQ ID NO 58
<211> LENGTH: 60
<212> TYPE: DNA
<213> ORGANISM: Artificial Sequence
<220> FEATURE:
<223> OTHER INFORMATION: Synthesized

<400> SEQUENCE: 58
ggtcatgctt ctgattggtg gtctgcgtgc acgtcacact atcggtgcat acgaggatct 60

<210> SEQ ID NO 59
<211> LENGTH: 60
<212> TYPE: DNA

<213> ORGANISM: Artificial Sequence
<220> FEATURE:
<223> OTHER INFORMATION: Synthesized

<400> SEQUENCE: 59
gtgtgcgaac tcgtaaccag tagcaacaat ctccataccc agatcctcgt atgcaccgat 60

<210> SEQ ID NO 60
<211> LENGTH: 60
<212> TYPE: DNA
<213> ORGANISM: Artificial Sequence
<220> FEATURE:
<223> OTHER INFORMATION: Synthesized

<400> SEQUENCE: 60
ctggttacga gttcgcacac aaggacgact acgagaagac cttccctgat gtcaaggagg 60

<210> SEQ ID NO 61
<211> LENGTH: 60
<212> TYPE: DNA
<213> ORGANISM: Artificial Sequence
<220> FEATURE:
<223> OTHER INFORMATION: Synthesized

<400> SEQUENCE: 61
tccagttcgt atgcagttgg atcatcgtac aggatagtac cctccttgac atcagggaag 60

<210> SEQ ID NO 62
<211> LENGTH: 60
<212> TYPE: DNA
<213> ORGANISM: Artificial Sequence
<220> FEATURE:
<223> OTHER INFORMATION: Synthesized

<400> SEQUENCE: 62
ccaactgcat acgaactgga ggaacttgca caacgtctga acatcgactt gatgggtgct 60

<210> SEQ ID NO 63
<211> LENGTH: 60
<212> TYPE: DNA
<213> ORGANISM: Artificial Sequence
<220> FEATURE:
<223> OTHER INFORMATION: Synthesized

<400> SEQUENCE: 63
gaatacccat cttgtggtag acgtacttct ccttgacacc agcacccatc aagtcgatgt 60

<210> SEQ ID NO 64
<211> LENGTH: 60
<212> TYPE: DNA
<213> ORGANISM: Artificial Sequence
<220> FEATURE:
<223> OTHER INFORMATION: Synthesized

<400> SEQUENCE: 64
ctaccacaag atgggtattc cattccgtca gatgcactcc tgggactact ctggtcctta 60

<210> SEQ ID NO 65
<211> LENGTH: 60
<212> TYPE: DNA
<213> ORGANISM: Artificial Sequence
<220> FEATURE:
<223> OTHER INFORMATION: Synthesized

<400> SEQUENCE: 65
catgtcacgt gcgaagattt tgaaaccgtc gaaaccatgg taaggaccag agtagtccca 60

<210> SEQ ID NO 66
<211> LENGTH: 60
<212> TYPE: DNA
<213> ORGANISM: Artificial Sequence
<220> FEATURE:
<223> OTHER INFORMATION: Synthesized

<400> SEQUENCE: 66
aaatcttcgc acgtgacatg gatatgacca tcaactcacc tgtttggtct ctgcttccat 60

<210> SEQ ID NO 67
<211> LENGTH: 49
<212> TYPE: DNA
<213> ORGANISM: Artificial Sequence
<220> FEATURE:
<223> OTHER INFORMATION: Synthesized

<400> SEQUENCE: 67
ttagacagga acctcagcag tctgacgtga tggaagcaga gaccaaaca 49

<210> SEQ ID NO 68
<211> LENGTH: 60
<212> TYPE: DNA
<213> ORGANISM: Artificial Sequence
<220> FEATURE:
<223> OTHER INFORMATION: Synthesized

<400> SEQUENCE: 68
atgtctgaac gtcctaacat tgttgatcac aaccaactgt tccgtcagga caagtacgtt 60

<210> SEQ ID NO 69
<211> LENGTH: 60
<212> TYPE: DNA
<213> ORGANISM: Artificial Sequence
<220> FEATURE:
<223> OTHER INFORMATION: Synthesized

<400> SEQUENCE: 69
aacatggtgc ctcgaatgca cgcttctctt cacgttgacg aacgtacttg tcctgacgga 60

<210> SEQ ID NO 70
<211> LENGTH: 60
<212> TYPE: DNA
<213> ORGANISM: Artificial Sequence
<220> FEATURE:
<223> OTHER INFORMATION: Synthesized

<400> SEQUENCE: 70
tgcattcgag gcaccatgtt cacctgagga ggtcactgat actctggagt acaccaagac 60

<210> SEQ ID NO 71
<211> LENGTH: 60
<212> TYPE: DNA
<213> ORGANISM: Artificial Sequence
<220> FEATURE:
<223> OTHER INFORMATION: Synthesized

<400> SEQUENCE: 71
aacagcagta cgtgcgaagt tcttgtcctt gtactccttg gtcttggtgt actccagagt 60

<210> SEQ ID NO 72
<211> LENGTH: 60
<212> TYPE: DNA
<213> ORGANISM: Artificial Sequence
<220> FEATURE:

<223> OTHER INFORMATION: Synthesized

<400> SEQUENCE: 72
acttcgcacg tactgctgtt gtcgtcaacc ctgcaaaggc atgtcaacca ctgggtgctg 60

<210> SEQ ID NO 73
<211> LENGTH: 60
<212> TYPE: DNA
<213> ORGANISM: Artificial Sequence
<220> FEATURE:
<223> OTHER INFORMATION: Synthesized

<400> SEQUENCE: 73
atgaatggaa gggtcttctc gaaacccagt gcagccatga cagcacccag tggttgacat 60

<210> SEQ ID NO 74
<211> LENGTH: 60
<212> TYPE: DNA
<213> ORGANISM: Artificial Sequence
<220> FEATURE:
<223> OTHER INFORMATION: Synthesized

<400> SEQUENCE: 74
gagaagaccc ttccattcat ccatggttca cagggttgca ctgcatactt ccgttctcac 60

<210> SEQ ID NO 75
<211> LENGTH: 60
<212> TYPE: DNA
<213> ORGANISM: Artificial Sequence
<220> FEATURE:
<223> OTHER INFORMATION: Synthesized

<400> SEQUENCE: 75
tggagacagc agggacaggt tccttgaagt gacgtgcaag gtgagaacgg aagtatgcag 60

<210> SEQ ID NO 76
<211> LENGTH: 60
<212> TYPE: DNA
<213> ORGANISM: Artificial Sequence
<220> FEATURE:
<223> OTHER INFORMATION: Synthesized

<400> SEQUENCE: 76
acctgtccct gctgtctcca cctccatgac tgaggacgct gctgtcttcg gtggtatgcg 60

<210> SEQ ID NO 77
<211> LENGTH: 60
<212> TYPE: DNA
<213> ORGANISM: Artificial Sequence
<220> FEATURE:
<223> OTHER INFORMATION: Synthesized

<400> SEQUENCE: 77
atacagtgca atgcagttct cgataccatc gatgaggtta cgcataccac cgaagacagc 60

<210> SEQ ID NO 78
<211> LENGTH: 60
<212> TYPE: DNA
<213> ORGANISM: Artificial Sequence
<220> FEATURE:
<223> OTHER INFORMATION: Synthesized

<400> SEQUENCE: 78
agaactgcat tgcactgtat caacctgaga tgattgctgt ctgcaccacc tgtatggctg 60

```
<210> SEQ ID NO 79
<211> LENGTH: 60
<212> TYPE: DNA
<213> ORGANISM: Artificial Sequence
<220> FEATURE:
<223> OTHER INFORMATION: Synthesized

<400> SEQUENCE: 79

gcgttggcaa ggaatgcaga cagatcatca ccaatgacct cagccataca ggtggtgcag     60


<210> SEQ ID NO 80
<211> LENGTH: 60
<212> TYPE: DNA
<213> ORGANISM: Artificial Sequence
<220> FEATURE:
<223> OTHER INFORMATION: Synthesized

<400> SEQUENCE: 80

tctgcattcc ttgccaacgc acgtcaggag ggtgtccttc ctgaggacat gcctgttcca     60


<210> SEQ ID NO 81
<211> LENGTH: 60
<212> TYPE: DNA
<213> ORGANISM: Artificial Sequence
<220> FEATURE:
<223> OTHER INFORMATION: Synthesized

<400> SEQUENCE: 81

cagtgatgtg tgaaccagag aaggatggag tgtttgcgaa tggaacaggc atgtcctcag     60


<210> SEQ ID NO 82
<211> LENGTH: 60
<212> TYPE: DNA
<213> ORGANISM: Artificial Sequence
<220> FEATURE:
<223> OTHER INFORMATION: Synthesized

<400> SEQUENCE: 82

ctctggttca cacatcactg gttacgatgc aatgctgcgt tctgttctgg aaaccctgta     60


<210> SEQ ID NO 83
<211> LENGTH: 60
<212> TYPE: DNA
<213> ORGANISM: Artificial Sequence
<220> FEATURE:
<223> OTHER INFORMATION: Synthesized

<400> SEQUENCE: 83

cagttcatga ccaggttgtg cagtacgacc agacttgttg tacagggttt ccagaacaga     60


<210> SEQ ID NO 84
<211> LENGTH: 60
<212> TYPE: DNA
<213> ORGANISM: Artificial Sequence
<220> FEATURE:
<223> OTHER INFORMATION: Synthesized

<400> SEQUENCE: 84

cacaacctgg tcatgaactg aagctgaacg tcctgcttgg tttcgatggt tacactggta     60


<210> SEQ ID NO 85
<211> LENGTH: 60
<212> TYPE: DNA
<213> ORGANISM: Artificial Sequence
<220> FEATURE:
<223> OTHER INFORMATION: Synthesized
```

<400> SEQUENCE: 85
gcaccgaaca taccaagcat acgacgcatc tcagcgaagt taccagtgta accatcgaaa 60

<210> SEQ ID NO 86
<211> LENGTH: 60
<212> TYPE: DNA
<213> ORGANISM: Artificial Sequence
<220> FEATURE:
<223> OTHER INFORMATION: Synthesized

<400> SEQUENCE: 86
atgcttggta tgttcggtgc tacctacacc atccttggtg atcattcctc caacttcgac 60

<210> SEQ ID NO 87
<211> LENGTH: 60
<212> TYPE: DNA
<213> ORGANISM: Artificial Sequence
<220> FEATURE:
<223> OTHER INFORMATION: Synthesized

<400> SEQUENCE: 87
taccaccata gtagtaggag tactcaccag ttgcaccaga gtcgaagttg gaggaatgat 60

<210> SEQ ID NO 88
<211> LENGTH: 60
<212> TYPE: DNA
<213> ORGANISM: Artificial Sequence
<220> FEATURE:
<223> OTHER INFORMATION: Synthesized

<400> SEQUENCE: 88
ctcctactac tatggtggta ctccacttga ggatgttcct aaggctgctg atgctgctgg 60

<210> SEQ ID NO 89
<211> LENGTH: 60
<212> TYPE: DNA
<213> ORGANISM: Artificial Sequence
<220> FEATURE:
<223> OTHER INFORMATION: Synthesized

<400> SEQUENCE: 89
aagagtctta cgaagtgagt actgctggat tgccagagta ccagcagcat cagcagcctt 60

<210> SEQ ID NO 90
<211> LENGTH: 60
<212> TYPE: DNA
<213> ORGANISM: Artificial Sequence
<220> FEATURE:
<223> OTHER INFORMATION: Synthesized

<400> SEQUENCE: 90
actcacttcg taagactctt ggttacatga agcaaacttg gggtcagcag gtctcatcca 60

<210> SEQ ID NO 91
<211> LENGTH: 60
<212> TYPE: DNA
<213> ORGANISM: Artificial Sequence
<220> FEATURE:
<223> OTHER INFORMATION: Synthesized

<400> SEQUENCE: 91
agcagacgat cagtagcacg gatacccagt ggagtggaga tggatgagac ctgctgaccc 60

<210> SEQ ID NO 92
<211> LENGTH: 60

<212> TYPE: DNA
<213> ORGANISM: Artificial Sequence
<220> FEATURE:
<223> OTHER INFORMATION: Synthesized

<400> SEQUENCE: 92
cgtgctactg atcgtctgct tgaggaaatc tcacgtctgt ctggtcgtga gatccctgag 60

<210> SEQ ID NO 93
<211> LENGTH: 60
<212> TYPE: DNA
<213> ORGANISM: Artificial Sequence
<220> FEATURE:
<223> OTHER INFORMATION: Synthesized

<400> SEQUENCE: 93
tcattgcatc gacgatacgt gcacgttcct gcttcagtgc ctcagggatc tcacgaccag 60

<210> SEQ ID NO 94
<211> LENGTH: 60
<212> TYPE: DNA
<213> ORGANISM: Artificial Sequence
<220> FEATURE:
<223> OTHER INFORMATION: Synthesized

<400> SEQUENCE: 94
acgtatcgtc gatgcaatga tggactcaca tgcatacctg catggtaagc gtgttgctat 60

<210> SEQ ID NO 95
<211> LENGTH: 60
<212> TYPE: DNA
<213> ORGANISM: Artificial Sequence
<220> FEATURE:
<223> OTHER INFORMATION: Synthesized

<400> SEQUENCE: 95
gaaaccgatc agaccaatga gcatgtcagg atcaccagcc atagcaacac gcttaccatg 60

<210> SEQ ID NO 96
<211> LENGTH: 60
<212> TYPE: DNA
<213> ORGANISM: Artificial Sequence
<220> FEATURE:
<223> OTHER INFORMATION: Synthesized

<400> SEQUENCE: 96
tcattggtct gatcggtttc tgtctggaac tgggtatgga acctgtccac attgtctgct 60

<210> SEQ ID NO 97
<211> LENGTH: 60
<212> TYPE: DNA
<213> ORGANISM: Artificial Sequence
<220> FEATURE:
<223> OTHER INFORMATION: Synthesized

<400> SEQUENCE: 97
agaagctcag cttccttctc gaacttacga tcaccgttgg agcagacaat gtggacaggt 60

<210> SEQ ID NO 98
<211> LENGTH: 60
<212> TYPE: DNA
<213> ORGANISM: Artificial Sequence
<220> FEATURE:
<223> OTHER INFORMATION: Synthesized

<400> SEQUENCE: 98
gagaaggaag ctgagcttct tctgaagtcc tcaccatacg gtgctgaagc aaccgttcac 60

<210> SEQ ID NO 99
<211> LENGTH: 60
<212> TYPE: DNA
<213> ORGANISM: Artificial Sequence
<220> FEATURE:
<223> OTHER INFORMATION: Synthesized

<400> SEQUENCE: 99
ggaacagcag agaacgcatg tgccacagat cctgaccaga gtgaacggtt gcttcagcac 60

<210> SEQ ID NO 100
<211> LENGTH: 60
<212> TYPE: DNA
<213> ORGANISM: Artificial Sequence
<220> FEATURE:
<223> OTHER INFORMATION: Synthesized

<400> SEQUENCE: 100
catgcgttct ctgctgttcc aggaccctgt tgatctggca atcggttcat cacatctgaa 60

<210> SEQ ID NO 101
<211> LENGTH: 60
<212> TYPE: DNA
<213> ORGANISM: Artificial Sequence
<220> FEATURE:
<223> OTHER INFORMATION: Synthesized

<400> SEQUENCE: 101
aacacgaagc agagggatct cagcctcctt ggcagcgaac ttcagatgtg atgaaccgat 60

<210> SEQ ID NO 102
<211> LENGTH: 60
<212> TYPE: DNA
<213> ORGANISM: Artificial Sequence
<220> FEATURE:
<223> OTHER INFORMATION: Synthesized

<400> SEQUENCE: 102
agatccctct gcttcgtgtt ggtttcccaa tcttcgatcg tcatcacctg catcgttacc 60

<210> SEQ ID NO 103
<211> LENGTH: 60
<212> TYPE: DNA
<213> ORGANISM: Artificial Sequence
<220> FEATURE:
<223> OTHER INFORMATION: Synthesized

<400> SEQUENCE: 103
tgagtgagca ggttcagtgc accctgataa ccaatgattg ggtaacgatg caggtgatga 60

<210> SEQ ID NO 104
<211> LENGTH: 60
<212> TYPE: DNA
<213> ORGANISM: Artificial Sequence
<220> FEATURE:
<223> OTHER INFORMATION: Synthesized

<400> SEQUENCE: 104
gcactgaacc tgctcactca gttcgtcaac accatcctcg acgttatgga ggaacaggca 60

<210> SEQ ID NO 105
<211> LENGTH: 50
<212> TYPE: DNA
<213> ORGANISM: Artificial Sequence
<220> FEATURE:
<223> OTHER INFORMATION: Synthesized

<400> SEQUENCE: 105
ttaacgaacc aggtcgaagg agtgatcagg tgcctgttcc tccataacgt 50

<210> SEQ ID NO 106
<211> LENGTH: 60
<212> TYPE: DNA
<213> ORGANISM: Artificial Sequence
<220> FEATURE:
<223> OTHER INFORMATION: Synthesized

<400> SEQUENCE: 106
atggactcac ttgctgatct ctccgaaact ccactggcac tggaaactct tcgtcgtcat 60

<210> SEQ ID NO 107
<211> LENGTH: 60
<212> TYPE: DNA
<213> ORGANISM: Artificial Sequence
<220> FEATURE:
<223> OTHER INFORMATION: Synthesized

<400> SEQUENCE: 107
tacgtgcgaa gtaacgatgt gcctcttcgt tgtagcatgg atgacgacga agagtttcca 60

<210> SEQ ID NO 108
<211> LENGTH: 60
<212> TYPE: DNA
<213> ORGANISM: Artificial Sequence
<220> FEATURE:
<223> OTHER INFORMATION: Synthesized

<400> SEQUENCE: 108
acatcgttac ttcgcacgta tccatcttcc tgttgcacct gcttgcaaca tccagtgtca 60

<210> SEQ ID NO 109
<211> LENGTH: 60
<212> TYPE: DNA
<213> ORGANISM: Artificial Sequence
<220> FEATURE:
<223> OTHER INFORMATION: Synthesized

<400> SEQUENCE: 109
acgtgactcg ttgacacagt cgaacttacg gttgcagtag tgacactgga tgttgcaagc 60

<210> SEQ ID NO 110
<211> LENGTH: 60
<212> TYPE: DNA
<213> ORGANISM: Artificial Sequence
<220> FEATURE:
<223> OTHER INFORMATION: Synthesized

<400> SEQUENCE: 110
actgtgtcaa cgagtcacgt cctggtgtcg tctctgaact gctgactcct gaacaggctg 60

<210> SEQ ID NO 111
<211> LENGTH: 60
<212> TYPE: DNA
<213> ORGANISM: Artificial Sequence
<220> FEATURE:
<223> OTHER INFORMATION: Synthesized

<400> SEQUENCE: 111
agctgcatca gctgtgcagc aacaccgtag gtcttggatg cagcctgttc aggagtcagc 60

<210> SEQ ID NO 112
<211> LENGTH: 60
<212> TYPE: DNA
<213> ORGANISM: Artificial Sequence
<220> FEATURE:
<223> OTHER INFORMATION: Synthesized

<400> SEQUENCE: 112
gctgcacagc tgatgcagct gtctgttgtt ggtatcgctg gtcctggtga tccactggca 60

<210> SEQ ID NO 113
<211> LENGTH: 60
<212> TYPE: DNA
<213> ORGANISM: Artificial Sequence
<220> FEATURE:
<223> OTHER INFORMATION: Synthesized

<400> SEQUENCE: 113
cacgaacacg acggaaggtg tcgaaggttg cctcagcgtt tgccagtgga tcaccaggac 60

<210> SEQ ID NO 114
<211> LENGTH: 60
<212> TYPE: DNA
<213> ORGANISM: Artificial Sequence
<220> FEATURE:
<223> OTHER INFORMATION: Synthesized

<400> SEQUENCE: 114
caccttccgt cgtgttcgtg agactgtcaa ggatgtcatc ttctgtctct caaccaacgg 60

<210> SEQ ID NO 115
<211> LENGTH: 60
<212> TYPE: DNA
<213> ORGANISM: Artificial Sequence
<220> FEATURE:
<223> OTHER INFORMATION: Synthesized

<400> SEQUENCE: 115
cagttcgacg atacgatcga tgtgacgaat cagagtcaga ccgttggttg agagacagaa 60

<210> SEQ ID NO 116
<211> LENGTH: 60
<212> TYPE: DNA
<213> ORGANISM: Artificial Sequence
<220> FEATURE:
<223> OTHER INFORMATION: Synthesized

<400> SEQUENCE: 116
tcgatcgtat cgtcgaactg ggtatctcac acgtcaccat caccatcaac gctgtcgatc 60

<210> SEQ ID NO 117
<211> LENGTH: 60
<212> TYPE: DNA
<213> ORGANISM: Artificial Sequence
<220> FEATURE:
<223> OTHER INFORMATION: Synthesized

<400> SEQUENCE: 117
tcatcataga cccaaccgta gatacgtgaa ccaacaacag gatcgacagc gttgatggtg 60

<210> SEQ ID NO 118
<211> LENGTH: 60
<212> TYPE: DNA
<213> ORGANISM: Artificial Sequence
<220> FEATURE:
<223> OTHER INFORMATION: Synthesized

<400> SEQUENCE: 118
tacggttggg tctatgatga aggtaaacgt tacgctggtg aggaggctgc acgtctgttg 60

<210> SEQ ID NO 119
<211> LENGTH: 60
<212> TYPE: DNA
<213> ORGANISM: Artificial Sequence
<220> FEATURE:
<223> OTHER INFORMATION: Synthesized

<400> SEQUENCE: 119
gtgatgccag catcttcaga ccagccagct gacgatcgat caacagacgt gcagcctcct 60

<210> SEQ ID NO 120
<211> LENGTH: 60
<212> TYPE: DNA
<213> ORGANISM: Artificial Sequence
<220> FEATURE:
<223> OTHER INFORMATION: Synthesized

<400> SEQUENCE: 120
tctgaagatg ctggcatcac gtggtgtctt gtgcaaggtc aactctgtcc tgattcctga 60

<210> SEQ ID NO 121
<211> LENGTH: 60
<212> TYPE: DNA
<213> ORGANISM: Artificial Sequence
<220> FEATURE:
<223> OTHER INFORMATION: Synthesized

<400> SEQUENCE: 121
gacaacacgt gcaacctcag gaagatgtgc atcgttgact tcaggaatca ggacagagtt 60

<210> SEQ ID NO 122
<211> LENGTH: 60
<212> TYPE: DNA
<213> ORGANISM: Artificial Sequence
<220> FEATURE:
<223> OTHER INFORMATION: Synthesized

<400> SEQUENCE: 122
ctgaggttgc acgtgttgtc aaggaacatg gtgctgttct gcacaacatc atgccactca 60

<210> SEQ ID NO 123
<211> LENGTH: 60
<212> TYPE: DNA
<213> ORGANISM: Artificial Sequence
<220> FEATURE:
<223> OTHER INFORMATION: Synthesized

<400> SEQUENCE: 123
cgcatacctt cctgttcgta acgtgaacca ggtgcaatga tgagtggcat gatgttgtgc 60

<210> SEQ ID NO 124
<211> LENGTH: 60
<212> TYPE: DNA
<213> ORGANISM: Artificial Sequence
<220> FEATURE:
<223> OTHER INFORMATION: Synthesized

<400> SEQUENCE: 124
tacgaacagg aaggtatgcg tgcaccacgt ccacgtctgg ttcgtcagct tcaggaacaa 60

<210> SEQ ID NO 125

<211> LENGTH: 60
<212> TYPE: DNA
<213> ORGANISM: Artificial Sequence
<220> FEATURE:
<223> OTHER INFORMATION: Synthesized

<400> SEQUENCE: 125
gacgacagtg acgcatgatg acagcaccag cttcagcaca ttgttcctga agctgacgaa 60

<210> SEQ ID NO 126
<211> LENGTH: 60
<212> TYPE: DNA
<213> ORGANISM: Artificial Sequence
<220> FEATURE:
<223> OTHER INFORMATION: Synthesized

<400> SEQUENCE: 126
catcatgcgt cactgtcgtc agtgtcgtgc tgatgcaatc ggtctgctgg gtgaggaccg 60

<210> SEQ ID NO 127
<211> LENGTH: 60
<212> TYPE: DNA
<213> ORGANISM: Artificial Sequence
<220> FEATURE:
<223> OTHER INFORMATION: Synthesized

<400> SEQUENCE: 127
tggtgcagca gcaatgttct cccaagtgaa gtcctggtta cggtcctcac ccagcagacc 60

<210> SEQ ID NO 128
<211> LENGTH: 60
<212> TYPE: DNA
<213> ORGANISM: Artificial Sequence
<220> FEATURE:
<223> OTHER INFORMATION: Synthesized

<400> SEQUENCE: 128
agaacattgc tgctgcacca cctatggatg aagaggcacg tgcacagttc cagaaggaac 60

<210> SEQ ID NO 129
<211> LENGTH: 60
<212> TYPE: DNA
<213> ORGANISM: Artificial Sequence
<220> FEATURE:
<223> OTHER INFORMATION: Synthesized

<400> SEQUENCE: 129
ccctccttac gttccatacg aacacgaacc ttctcatcca gttccttctg gaactgtgca 60

<210> SEQ ID NO 130
<211> LENGTH: 60
<212> TYPE: DNA
<213> ORGANISM: Artificial Sequence
<220> FEATURE:
<223> OTHER INFORMATION: Synthesized

<400> SEQUENCE: 130
cgtatggaac gtaaggaggg tcagtctcac cacaagcaac catcaaccgg tgctggttgt 60

<210> SEQ ID NO 131
<211> LENGTH: 60
<212> TYPE: DNA
<213> ORGANISM: Artificial Sequence
<220> FEATURE:
<223> OTHER INFORMATION: Synthesized

<400> SEQUENCE: 131
tgaaggatgc ttcaggcttg tcaccagaca gtggacaaga acaaccagca ccggttgatg 60

<210> SEQ ID NO 132
<211> LENGTH: 60
<212> TYPE: DNA
<213> ORGANISM: Artificial Sequence
<220> FEATURE:
<223> OTHER INFORMATION: Synthesized

<400> SEQUENCE: 132
caagcctgaa gcatccttca cctccaagcc tgtcttgatc gctgttgcat cacgtggtgg 60

<210> SEQ ID NO 133
<211> LENGTH: 60
<212> TYPE: DNA
<213> ORGANISM: Artificial Sequence
<220> FEATURE:
<223> OTHER INFORMATION: Synthesized

<400> SEQUENCE: 133
gaactccttt gcacgaccga agtgctggtt gaccttacca ccaccacgtg atgcaacagc 60

<210> SEQ ID NO 134
<211> LENGTH: 60
<212> TYPE: DNA
<213> ORGANISM: Artificial Sequence
<220> FEATURE:
<223> OTHER INFORMATION: Synthesized

<400> SEQUENCE: 134
tcggtcgtgc aaaggagttc atgatctacg aatctgatgg tactatcgtc aacttcatcg 60

<210> SEQ ID NO 135
<211> LENGTH: 60
<212> TYPE: DNA
<213> ORGANISM: Artificial Sequence
<220> FEATURE:
<223> OTHER INFORMATION: Synthesized

<400> SEQUENCE: 135
tcagccttac catgacagta ggactggacc ttacggatac cgatgaagtt gacgatagta 60

<210> SEQ ID NO 136
<211> LENGTH: 60
<212> TYPE: DNA
<213> ORGANISM: Artificial Sequence
<220> FEATURE:
<223> OTHER INFORMATION: Synthesized

<400> SEQUENCE: 136
tactgtcatg gtaaggctga ctgcaatggt gacaaggctg agaccatcaa ggagatcctg 60

<210> SEQ ID NO 137
<211> LENGTH: 60
<212> TYPE: DNA
<213> ORGANISM: Artificial Sequence
<220> FEATURE:
<223> OTHER INFORMATION: Synthesized

<400> SEQUENCE: 137
taccggatga cagcagcagt gcacagtcat gaaccattga caggatctcc ttgatggtct 60

<210> SEQ ID NO 138
<211> LENGTH: 60
<212> TYPE: DNA

<213> ORGANISM: Artificial Sequence
<220> FEATURE:
<223> OTHER INFORMATION: Synthesized

<400> SEQUENCE: 138
actgctgctg tcatccggta tcggtgaagc accaaaggag gcactccagg aagctggtgt 60

<210> SEQ ID NO 139
<211> LENGTH: 60
<212> TYPE: DNA
<213> ORGANISM: Artificial Sequence
<220> FEATURE:
<223> OTHER INFORMATION: Synthesized

<400> SEQUENCE: 139
aacagactcc tcgatgtcac caccacagac gattggcagg acaccagctt cctggagtgc 60

<210> SEQ ID NO 140
<211> LENGTH: 60
<212> TYPE: DNA
<213> ORGANISM: Artificial Sequence
<220> FEATURE:
<223> OTHER INFORMATION: Synthesized

<400> SEQUENCE: 140
gtgacatcga ggagtctgtt ctggagtacg tcaagttcct gcgttacatg taccctgtcc 60

<210> SEQ ID NO 141
<211> LENGTH: 60
<212> TYPE: DNA
<213> ORGANISM: Artificial Sequence
<220> FEATURE:
<223> OTHER INFORMATION: Synthesized

<400> SEQUENCE: 141
cccttgacac ccttgttacg cttggaaccc ttaccagtct ggacagggta catgtaacgc 60

<210> SEQ ID NO 142
<211> LENGTH: 60
<212> TYPE: DNA
<213> ORGANISM: Artificial Sequence
<220> FEATURE:
<223> OTHER INFORMATION: Synthesized

<400> SEQUENCE: 142
ttaaccaccg aagtgttcga taggcaagtc ggagtgatta cccttgacac ccttgttacg 60

<210> SEQ ID NO 143
<211> LENGTH: 60
<212> TYPE: DNA
<213> ORGANISM: Artificial Sequence
<220> FEATURE:
<223> OTHER INFORMATION: Synthesized

<400> SEQUENCE: 143
atggaaccag ctgtctccaa tggtcgtctt gaggtctcct gtggtaacaa gattcctaag 60

<210> SEQ ID NO 144
<211> LENGTH: 60
<212> TYPE: DNA
<213> ORGANISM: Artificial Sequence
<220> FEATURE:
<223> OTHER INFORMATION: Synthesized

<400> SEQUENCE: 144
cagatgcttc accaggaaca ggacgtggac atggagtaga cttaggaatc ttgttaccac 60

<210> SEQ ID NO 145
<211> LENGTH: 60
<212> TYPE: DNA
<213> ORGANISM: Artificial Sequence
<220> FEATURE:
<223> OTHER INFORMATION: Synthesized

<400> SEQUENCE: 145
tgttcctggt gaagcatctg gtggttgctc attcgatggt gcacagatca ctctgattcc 60

<210> SEQ ID NO 146
<211> LENGTH: 60
<212> TYPE: DNA
<213> ORGANISM: Artificial Sequence
<220> FEATURE:
<223> OTHER INFORMATION: Synthesized

<400> SEQUENCE: 146
tgcgattgga ccatgaacaa gatgtgcagc atcagcgatt ggaatcagag tgatctgtgc 60

<210> SEQ ID NO 147
<211> LENGTH: 60
<212> TYPE: DNA
<213> ORGANISM: Artificial Sequence
<220> FEATURE:
<223> OTHER INFORMATION: Synthesized

<400> SEQUENCE: 147
ttgttcatgg tccaatcgca tgtcttggta actcttggga gtcacgtggt tcactgtcat 60

<210> SEQ ID NO 148
<211> LENGTH: 60
<212> TYPE: DNA
<213> ORGANISM: Artificial Sequence
<220> FEATURE:
<223> OTHER INFORMATION: Synthesized

<400> SEQUENCE: 148
aggtcagtag tgaaaccgta tgcggagagt tcaggaccag atgacagtga accacgtgac 60

<210> SEQ ID NO 149
<211> LENGTH: 60
<212> TYPE: DNA
<213> ORGANISM: Artificial Sequence
<220> FEATURE:
<223> OTHER INFORMATION: Synthesized

<400> SEQUENCE: 149
tacggtttca ctactgacct gggtgagcag gacatcatct tcggttctga acagaagctg 60

<210> SEQ ID NO 150
<211> LENGTH: 60
<212> TYPE: DNA
<213> ORGANISM: Artificial Sequence
<220> FEATURE:
<223> OTHER INFORMATION: Synthesized

<400> SEQUENCE: 150
gtggtgcgaa acgtgagacg atgtaacgga ttgactcatg cagcttctgt tcagaaccga 60

<210> SEQ ID NO 151
<211> LENGTH: 60
<212> TYPE: DNA
<213> ORGANISM: Artificial Sequence
<220> FEATURE:

<223> OTHER INFORMATION: Synthesized

<400> SEQUENCE: 151
cgtctcacgt ttcgcaccac ctgctgtctt cgtctacacc acctgtgtca ctgcactcac 60

<210> SEQ ID NO 152
<211> LENGTH: 60
<212> TYPE: DNA
<213> ORGANISM: Artificial Sequence
<220> FEATURE:
<223> OTHER INFORMATION: Synthesized

<400> SEQUENCE: 152
ttcagactca gccttgcaga caccttcgat gtcttcacca gtgagtgcag tgacacaggt 60

<210> SEQ ID NO 153
<211> LENGTH: 60
<212> TYPE: DNA
<213> ORGANISM: Artificial Sequence
<220> FEATURE:
<223> OTHER INFORMATION: Synthesized

<400> SEQUENCE: 153
tctgcaaggc tgagtctgaa cgtcttggta ctccaatcat ccctgtcaac tcacctggtt 60

<210> SEQ ID NO 154
<211> LENGTH: 60
<212> TYPE: DNA
<213> ORGANISM: Artificial Sequence
<220> FEATURE:
<223> OTHER INFORMATION: Synthesized

<400> SEQUENCE: 154
tcaccagcaa gacgagtacc aaggttcttg gaaccaacga aaccaggtga gttgacaggg 60

<210> SEQ ID NO 155
<211> LENGTH: 60
<212> TYPE: DNA
<213> ORGANISM: Artificial Sequence
<220> FEATURE:
<223> OTHER INFORMATION: Synthesized

<400> SEQUENCE: 155
ggtactcgtc ttgctggtga tgtcctgttc cagcacatca tcggttcaac cgaacctgaa 60

<210> SEQ ID NO 156
<211> LENGTH: 60
<212> TYPE: DNA
<213> ORGANISM: Artificial Sequence
<220> FEATURE:
<223> OTHER INFORMATION: primer

<400> SEQUENCE: 156
tgtactcacc aatgaggttg atgtcatgtg aggtggtctg ttcaggttcg gttgaaccga 60

<210> SEQ ID NO 157
<211> LENGTH: 60
<212> TYPE: DNA
<213> ORGANISM: Artificial Sequence
<220> FEATURE:
<223> OTHER INFORMATION: Synthesized

<400> SEQUENCE: 157
caacctcatt ggtgagtaca acatcgctgg tgagatgtgg cacattgaac gtctgatgca 60

<210> SEQ ID NO 158
<211> LENGTH: 60
<212> TYPE: DNA
<213> ORGANISM: Artificial Sequence
<220> FEATURE:
<223> OTHER INFORMATION: Synthesized

<400> SEQUENCE: 158
atcaccagtg atacgtgaca ggatggacat acctgcttgt tgcatcagac gttcaatgtg 60

<210> SEQ ID NO 159
<211> LENGTH: 60
<212> TYPE: DNA
<213> ORGANISM: Artificial Sequence
<220> FEATURE:
<223> OTHER INFORMATION: Synthesized

<400> SEQUENCE: 159
tgtcacgtat cactggtgat ggtcgtttcc gtgaagttgg ttgggcacat cgtgcaaagg 60

<210> SEQ ID NO 160
<211> LENGTH: 60
<212> TYPE: DNA
<213> ORGANISM: Artificial Sequence
<220> FEATURE:
<223> OTHER INFORMATION: Synthesized

<400> SEQUENCE: 160
gccagaccca gcagtgcacg tgagcagaca accatgttag cctttgcacg atgtgcccaa 60

<210> SEQ ID NO 161
<211> LENGTH: 60
<212> TYPE: DNA
<213> ORGANISM: Artificial Sequence
<220> FEATURE:
<223> OTHER INFORMATION: Synthesized

<400> SEQUENCE: 161
cgtgcactgc tgggtctggc tgttcagatg gaacgtaagt acggtatccc atacttcgaa 60

<210> SEQ ID NO 162
<211> LENGTH: 60
<212> TYPE: DNA
<213> ORGANISM: Artificial Sequence
<220> FEATURE:
<223> OTHER INFORMATION: Synthesized

<400> SEQUENCE: 162
gcaatgagta ggaggtctcc tttgcaccgt agaaggaacc ttcgaagtat gggataccgt 60

<210> SEQ ID NO 163
<211> LENGTH: 60
<212> TYPE: DNA
<213> ORGANISM: Artificial Sequence
<220> FEATURE:
<223> OTHER INFORMATION: Synthesized

<400> SEQUENCE: 163
ggagacctcc tactcattgc gtcagatggc atacctgact ggtgatcgtg atgttgagcg 60

<210> SEQ ID NO 164
<211> LENGTH: 60
<212> TYPE: DNA
<213> ORGANISM: Artificial Sequence
<220> FEATURE:
<223> OTHER INFORMATION: Synthesized

<400> SEQUENCE: 164
gagacgcatc tcctcacgtg cagcgagctt gtcaacacga cgctcaacat cacgatcacc 60

<210> SEQ ID NO 165
<211> LENGTH: 60
<212> TYPE: DNA
<213> ORGANISM: Artificial Sequence
<220> FEATURE:
<223> OTHER INFORMATION: Synthesized

<400> SEQUENCE: 165
cacgtgagga gatgcgtctc tcactggagc tggaaccata ccgtaagcag ctgaagggta 60

<210> SEQ ID NO 166
<211> LENGTH: 60
<212> TYPE: DNA
<213> ORGANISM: Artificial Sequence
<220> FEATURE:
<223> OTHER INFORMATION: Synthesized

<400> SEQUENCE: 166
gaccatgact tgacaccacc agtgtagagg acagcacgct tacccttcag ctgcttacgg 60

<210> SEQ ID NO 167
<211> LENGTH: 60
<212> TYPE: DNA
<213> ORGANISM: Artificial Sequence
<220> FEATURE:
<223> OTHER INFORMATION: Synthesized

<400> SEQUENCE: 167
ggtggtgtca agtcatggtc tgtcatcact gcactccagg agcttggtat caaggttgtt 60

<210> SEQ ID NO 168
<211> LENGTH: 60
<212> TYPE: DNA
<213> ORGANISM: Artificial Sequence
<220> FEATURE:
<223> OTHER INFORMATION: Synthesized

<400> SEQUENCE: 168
gtgagacatc ctcagcagtt gacttgttag taccgacacc aacaaccttg ataccaagct 60

<210> SEQ ID NO 169
<211> LENGTH: 60
<212> TYPE: DNA
<213> ORGANISM: Artificial Sequence
<220> FEATURE:
<223> OTHER INFORMATION: Synthesized

<400> SEQUENCE: 169
aactgctgag gatgtctcac gtatcgctga tcgtattggt gatgatgctg agtacattcc 60

<210> SEQ ID NO 170
<211> LENGTH: 60
<212> TYPE: DNA
<213> ORGANISM: Artificial Sequence
<220> FEATURE:
<223> OTHER INFORMATION: Synthesized

<400> SEQUENCE: 170
tgaacgaaca gtcttgagga tctgacgtgc accaccttca ggaatgtact cagcatcatc 60

<210> SEQ ID NO 171
<211> LENGTH: 60

<212> TYPE: DNA
<213> ORGANISM: Artificial Sequence
<220> FEATURE:
<223> OTHER INFORMATION: Synthesized

<400> SEQUENCE: 171
tcctcaagac tgttcgttca cgtaaggctg acatggtcat tgctggtggt cgtaacatgt 60

<210> SEQ ID NO 172
<211> LENGTH: 60
<212> TYPE: DNA
<213> ORGANISM: Artificial Sequence
<220> FEATURE:
<223> OTHER INFORMATION: Synthesized

<400> SEQUENCE: 172
ttgatgtcaa cgaatggaat ctgttccttc agtgccatgt acatgttacg accaccagca 60

<210> SEQ ID NO 173
<211> LENGTH: 60
<212> TYPE: DNA
<213> ORGANISM: Artificial Sequence
<220> FEATURE:
<223> OTHER INFORMATION: Synthesized

<400> SEQUENCE: 173
attccattcg ttgacatcaa ccaagaacgt cacaaggcat acgctggtta cgatggtctg 60

<210> SEQ ID NO 174
<211> LENGTH: 60
<212> TYPE: DNA
<213> ORGANISM: Artificial Sequence
<220> FEATURE:
<223> OTHER INFORMATION: Synthesized

<400> SEQUENCE: 174
gatgctgaag ggtatggaca agctgtttgg caagtgacaa cagaccatcg taaccagcgt 60

<210> SEQ ID NO 175
<211> LENGTH: 60
<212> TYPE: DNA
<213> ORGANISM: Artificial Sequence
<220> FEATURE:
<223> OTHER INFORMATION: Synthesized

<400> SEQUENCE: 175
tgtccatacc cttcagcatc ctgtctggga actgactgcc aaactggcac cttgggagga 60

<210> SEQ ID NO 176
<211> LENGTH: 42
<212> TYPE: DNA
<213> ORGANISM: Artificial Sequence
<220> FEATURE:
<223> OTHER INFORMATION: Synthesized

<400> SEQUENCE: 176
ttagtcagcg aactcagtct cctcctccca aggtgccagt tt 42

<210> SEQ ID NO 177
<211> LENGTH: 60
<212> TYPE: DNA
<213> ORGANISM: Artificial Sequence
<220> FEATURE:
<223> OTHER INFORMATION: Synthesized

<400> SEQUENCE: 177
atgcttatca agtctgcaac caagcctgtc tctgtcaatc cactcaaggt tggtcagcct 60

<210> SEQ ID NO 178
<211> LENGTH: 60
<212> TYPE: DNA
<213> ORGANISM: Artificial Sequence
<220> FEATURE:
<223> OTHER INFORMATION: Synthesized

<400> SEQUENCE: 178
ttgaacggta catacccctga agtgcaagaa caccaccaag aggctgacca accttgagtg 60

<210> SEQ ID NO 179
<211> LENGTH: 60
<212> TYPE: DNA
<213> ORGANISM: Artificial Sequence
<220> FEATURE:
<223> OTHER INFORMATION: Synthesized

<400> SEQUENCE: 179
tcagggtatg taccgttcaa tgccactgct gcatggtgca cagggttgct ctgcattctc 60

<210> SEQ ID NO 180
<211> LENGTH: 60
<212> TYPE: DNA
<213> ORGANISM: Artificial Sequence
<220> FEATURE:
<223> OTHER INFORMATION: Synthesized

<400> SEQUENCE: 180
agcgattggt tcacggaagt gacgagtcag cagtgccttg gagaatgcag agcaaccctg 60

<210> SEQ ID NO 181
<211> LENGTH: 60
<212> TYPE: DNA
<213> ORGANISM: Artificial Sequence
<220> FEATURE:
<223> OTHER INFORMATION: Synthesized

<400> SEQUENCE: 181
acttccgtga accaatcgct gttcagacct ctgcactgca agagatggat gtcatcttcg 60

<210> SEQ ID NO 182
<211> LENGTH: 60
<212> TYPE: DNA
<213> ORGANISM: Artificial Sequence
<220> FEATURE:
<223> OTHER INFORMATION: Synthesized

<400> SEQUENCE: 182
cagatgtgat ccagtgcctc ctccaggtta cgatcagcgt cgaagatgac atccatctct 60

<210> SEQ ID NO 183
<211> LENGTH: 60
<212> TYPE: DNA
<213> ORGANISM: Artificial Sequence
<220> FEATURE:
<223> OTHER INFORMATION: Synthesized

<400> SEQUENCE: 183
gaggcactgg atcacatctg gtccaagcat caccctgatg tcattggtgt catctctact 60

<210> SEQ ID NO 184
<211> LENGTH: 60
<212> TYPE: DNA
<213> ORGANISM: Artificial Sequence
<220> FEATURE:
<223> OTHER INFORMATION: Synthesized

<400> SEQUENCE: 184
cacgagactg gaaatcgaca ccagcaacct cagtgagtgc agtagagatg acaccaatga 60

<210> SEQ ID NO 185
<211> LENGTH: 60
<212> TYPE: DNA
<213> ORGANISM: Artificial Sequence
<220> FEATURE:
<223> OTHER INFORMATION: Synthesized

<400> SEQUENCE: 185
tgtcgatttc cagtctcgtg tcaaggcatt caagcgtgag cgtgcactga aggattctct 60

<210> SEQ ID NO 186
<211> LENGTH: 60
<212> TYPE: DNA
<213> ORGANISM: Artificial Sequence
<220> FEATURE:
<223> OTHER INFORMATION: Synthesized

<400> SEQUENCE: 186
cagagaacca tggaagtcag gaagtgagac agagaacagc agagaatcct tcagtgcacg 60

<210> SEQ ID NO 187
<211> LENGTH: 60
<212> TYPE: DNA
<213> ORGANISM: Artificial Sequence
<220> FEATURE:
<223> OTHER INFORMATION: Synthesized

<400> SEQUENCE: 187
ctgacttcca tggttctctg gagactggtt actcctctac cgtcgagtca ctcatggatg 60

<210> SEQ ID NO 188
<211> LENGTH: 60
<212> TYPE: DNA
<213> ORGANISM: Artificial Sequence
<220> FEATURE:
<223> OTHER INFORMATION: Synthesized

<400> SEQUENCE: 188
tgcttcttag gtgacttacc acctgccaaa ccgagaacag catccatgag tgactcgacg 60

<210> SEQ ID NO 189
<211> LENGTH: 60
<212> TYPE: DNA
<213> ORGANISM: Artificial Sequence
<220> FEATURE:
<223> OTHER INFORMATION: Synthesized

<400> SEQUENCE: 189
ggtaagtcac ctaagaagca acgtcgtact caggtcaacc tgcttcctgc atcctacctg 60

<210> SEQ ID NO 190
<211> LENGTH: 60
<212> TYPE: DNA
<213> ORGANISM: Artificial Sequence
<220> FEATURE:
<223> OTHER INFORMATION: Synthesized

<400> SEQUENCE: 190
atgcgatgat gtccttgatc tccatgacat caccagcagt caggtaggat gcaggaagca 60

<210> SEQ ID NO 191
<211> LENGTH: 60
<212> TYPE: DNA
<213> ORGANISM: Artificial Sequence
<220> FEATURE:
<223> OTHER INFORMATION: Synthesized

<400> SEQUENCE: 191
gatcaaggac atcatcgcat cctttggtct ggaggtcatc actcttcctg acatctccac 60

<210> SEQ ID NO 192
<211> LENGTH: 60
<212> TYPE: DNA
<213> ORGANISM: Artificial Sequence
<220> FEATURE:
<223> OTHER INFORMATION: Synthesized

<400> SEQUENCE: 192
cagtggtgag aaaccagtca gcagatgacc agacagggag gtggagatgt caggaagagt 60

<210> SEQ ID NO 193
<211> LENGTH: 60
<212> TYPE: DNA
<213> ORGANISM: Artificial Sequence
<220> FEATURE:
<223> OTHER INFORMATION: Synthesized

<400> SEQUENCE: 193
tgactggttt ctcaccactg actcgtggtg gtactccact ggactctgca tgtcagatgc 60

<210> SEQ ID NO 194
<211> LENGTH: 60
<212> TYPE: DNA
<213> ORGANISM: Artificial Sequence
<220> FEATURE:
<223> OTHER INFORMATION: Synthesized

<400> SEQUENCE: 194
tccatagatg caccgattgc gatagtacag gatgactcca gcatctgaca tgcagagtcc 60

<210> SEQ ID NO 195
<211> LENGTH: 60
<212> TYPE: DNA
<213> ORGANISM: Artificial Sequence
<220> FEATURE:
<223> OTHER INFORMATION: Synthesized

<400> SEQUENCE: 195
gcaatcggtg catctatgga acgtcctgca cgtcgtctga ctcatgctgc tggtatccca 60

<210> SEQ ID NO 196
<211> LENGTH: 60
<212> TYPE: DNA
<213> ORGANISM: Artificial Sequence
<220> FEATURE:
<223> OTHER INFORMATION: Synthesized

<400> SEQUENCE: 196
cagatgcagc cagaccagac agaccagcga acaggtgata tgggatacca gcagcatgag 60

<210> SEQ ID NO 197
<211> LENGTH: 60
<212> TYPE: DNA
<213> ORGANISM: Artificial Sequence
<220> FEATURE:
<223> OTHER INFORMATION: Synthesized

<400> SEQUENCE: 197
gtctggtctg gctgcatctg atgcattcat ccacttcctc cagaaaatct cacgtgaacc 60

<210> SEQ ID NO 198
<211> LENGTH: 60
<212> TYPE: DNA
<213> ORGANISM: Artificial Sequence
<220> FEATURE:
<223> OTHER INFORMATION: Synthesized

<400> SEQUENCE: 198
caacaggttc tcacgttgcc aacggaaacg aacaggtgca ggttcacgtg agattttctg 60

<210> SEQ ID NO 199
<211> LENGTH: 60
<212> TYPE: DNA
<213> ORGANISM: Artificial Sequence
<220> FEATURE:
<223> OTHER INFORMATION: Synthesized

<400> SEQUENCE: 199
ggcaacgtga gaacctgttg gattctatgc tggatgcaca cttctactac tctggtgcat 60

<210> SEQ ID NO 200
<211> LENGTH: 60
<212> TYPE: DNA
<213> ORGANISM: Artificial Sequence
<220> FEATURE:
<223> OTHER INFORMATION: Synthesized

<400> SEQUENCE: 200
gtagacagca tgtgatcagg ttcaagtgca acgacagcag atgcaccaga gtagtagaag 60

<210> SEQ ID NO 201
<211> LENGTH: 60
<212> TYPE: DNA
<213> ORGANISM: Artificial Sequence
<220> FEATURE:
<223> OTHER INFORMATION: Synthesized

<400> SEQUENCE: 201
cctgatcaca tgctgtctac tgctgcatgg ctggaggaga tgggtgtcga actgaagcgt 60

<210> SEQ ID NO 202
<211> LENGTH: 60
<212> TYPE: DNA
<213> ORGANISM: Artificial Sequence
<220> FEATURE:
<223> OTHER INFORMATION: Synthesized

<400> SEQUENCE: 202
cagtcttctg gagtgcagga gtagagcatg gagtgatcag acgcttcagt tcgacaccca 60

<210> SEQ ID NO 203
<211> LENGTH: 60
<212> TYPE: DNA
<213> ORGANISM: Artificial Sequence
<220> FEATURE:
<223> OTHER INFORMATION: Synthesized

<400> SEQUENCE: 203
tcctgcactc cagaagactg aacgtgaagt ctggattggt gatctggatg atgctgagga 60

<210> SEQ ID NO 204

<211> LENGTH: 60
<212> TYPE: DNA
<213> ORGANISM: Artificial Sequence
<220> FEATURE:
<223> OTHER INFORMATION: Synthesized

<400> SEQUENCE: 204
atgtgagttg gagatccaca gatcaacacc ctgtgcagac tcctcagcat catccagatc 60

<210> SEQ ID NO 205
<211> LENGTH: 60
<212> TYPE: DNA
<213> ORGANISM: Artificial Sequence
<220> FEATURE:
<223> OTHER INFORMATION: Synthesized

<400> SEQUENCE: 205
tgtggatctc caactcacat ggtcgtaagg gtgctgcacg tgctggtgca tcattcgttc 60

<210> SEQ ID NO 206
<211> LENGTH: 60
<212> TYPE: DNA
<213> ORGANISM: Artificial Sequence
<220> FEATURE:
<223> OTHER INFORMATION: Synthesized

<400> SEQUENCE: 206
gtgtgtgcac caagttcatc atagacaggc agaccagcag gaacgaatga tgcaccagca 60

<210> SEQ ID NO 207
<211> LENGTH: 60
<212> TYPE: DNA
<213> ORGANISM: Artificial Sequence
<220> FEATURE:
<223> OTHER INFORMATION: Synthesized

<400> SEQUENCE: 207
gatgaacttg gtgcacacac ttctgtctct gttggttatc gtggtactat ggaatgggtc 60

<210> SEQ ID NO 208
<211> LENGTH: 68
<212> TYPE: DNA
<213> ORGANISM: Artificial Sequence
<220> FEATURE:
<223> OTHER INFORMATION: Synthesized

<400> SEQUENCE: 208
ttaaccacca cgaccacgtt cagcgagcaa gacgttacca accttgttga cccattccat 60
agtaccac 68

<210> SEQ ID NO 209
<211> LENGTH: 60
<212> TYPE: DNA
<213> ORGANISM: Artificial Sequence
<220> FEATURE:
<223> OTHER INFORMATION: Synthesized

<400> SEQUENCE: 209
atgaaggttg cattcgcaac tgaagatggt gtccttgtca atgcacactt cggtcagtca 60

<210> SEQ ID NO 210
<211> LENGTH: 60
<212> TYPE: DNA
<213> ORGANISM: Artificial Sequence
<220> FEATURE:
<223> OTHER INFORMATION: Synthesized

<400> SEQUENCE: 210
ggacaccaga gtgacgaatc tcgaagatgg tgaacattgg tgactgaccg aagtgtgcat 60

<210> SEQ ID NO 211
<211> LENGTH: 60
<212> TYPE: DNA
<213> ORGANISM: Artificial Sequence
<220> FEATURE:
<223> OTHER INFORMATION: Synthesized

<400> SEQUENCE: 211
gattcgtcac tctggtgtcc agttcctgga acatcgtcgt atcgcactgg gttctgacga 60

<210> SEQ ID NO 212
<211> LENGTH: 60
<212> TYPE: DNA
<213> ORGANISM: Artificial Sequence
<220> FEATURE:
<223> OTHER INFORMATION: Synthesized

<400> SEQUENCE: 212
gatcagaccg atacgtgagg caatcttacc agcctcgttc tcgtcagaac ccagtgcgat 60

<210> SEQ ID NO 213
<211> LENGTH: 60
<212> TYPE: DNA
<213> ORGANISM: Artificial Sequence
<220> FEATURE:
<223> OTHER INFORMATION: Synthesized

<400> SEQUENCE: 213
cctcacgtat cggtctgatc gaggactgtg cactgatctt cctggttcag atcggtgcat 60

<210> SEQ ID NO 214
<211> LENGTH: 60
<212> TYPE: DNA
<213> ORGANISM: Artificial Sequence
<220> FEATURE:
<223> OTHER INFORMATION: Synthesized

<400> SEQUENCE: 214
acaggcatga tggtacgctt agtgacctgt gcagcagcag atgcaccgat ctgaaccagg 60

<210> SEQ ID NO 215
<211> LENGTH: 60
<212> TYPE: DNA
<213> ORGANISM: Artificial Sequence
<220> FEATURE:
<223> OTHER INFORMATION: Synthesized

<400> SEQUENCE: 215
aagcgtacca tcatgcctgt caaggtcgca ttcggttcta ccatcgagga acaggttcag 60

<210> SEQ ID NO 216
<211> LENGTH: 60
<212> TYPE: DNA
<213> ORGANISM: Artificial Sequence
<220> FEATURE:
<223> OTHER INFORMATION: Synthesized

<400> SEQUENCE: 216
gccacattgg tgggttacga gtcagcatgt tctgaagacg ctgaacctgt tcctcgatgg 60

<210> SEQ ID NO 217

```
<211> LENGTH: 60
<212> TYPE: DNA
<213> ORGANISM: Artificial Sequence
<220> FEATURE:
<223> OTHER INFORMATION: Synthesized

<400> SEQUENCE: 217

tcgtaaccca ccaatgtggc ttgcaaagat cctgcacgct gaggagggtt ctggtaaggc     60


<210> SEQ ID NO 218
<211> LENGTH: 30
<212> TYPE: DNA
<213> ORGANISM: Artificial Sequence
<220> FEATURE:
<223> OTHER INFORMATION: Synthesized

<400> SEQUENCE: 218

ttatgactca gccttaccag aaccctcctc                                      30


<210> SEQ ID NO 219
<211> LENGTH: 60
<212> TYPE: DNA
<213> ORGANISM: Artificial Sequence
<220> FEATURE:
<223> OTHER INFORMATION: Synthesized

<400> SEQUENCE: 219

atggttcaac ttcttgaaga ttcacgttat ggtcgtcagt tgaagctgct tggtgttgaa     60


<210> SEQ ID NO 220
<211> LENGTH: 60
<212> TYPE: DNA
<213> ORGANISM: Artificial Sequence
<220> FEATURE:
<223> OTHER INFORMATION: Synthesized

<400> SEQUENCE: 220

cagcaaccat aacggttgcc tgcttcagac gattctgacc ttcaacacca agcagcttca     60


<210> SEQ ID NO 221
<211> LENGTH: 60
<212> TYPE: DNA
<213> ORGANISM: Artificial Sequence
<220> FEATURE:
<223> OTHER INFORMATION: Synthesized

<400> SEQUENCE: 221

ggcaaccgtt atggttgctg gtatcggtgg tctgggtggt gctgctgcaa tgtatcttgc     60


<210> SEQ ID NO 222
<211> LENGTH: 60
<212> TYPE: DNA
<213> ORGANISM: Artificial Sequence
<220> FEATURE:
<223> OTHER INFORMATION: Synthesized

<400> SEQUENCE: 222

accctcatgt gccaagatca gcttaccaac accagcagca gcaagataca ttgcagcagc     60


<210> SEQ ID NO 223
<211> LENGTH: 60
<212> TYPE: DNA
<213> ORGANISM: Artificial Sequence
<220> FEATURE:
<223> OTHER INFORMATION: Synthesized

<400> SEQUENCE: 223
```

tgatcttggc acatgagggt gtcattcatc ttcctgatat gaatcgtcag gttctgatgg 60

<210> SEQ ID NO 224
<211> LENGTH: 60
<212> TYPE: DNA
<213> ORGANISM: Artificial Sequence
<220> FEATURE:
<223> OTHER INFORMATION: Synthesized

<400> SEQUENCE: 224
agtgcagtct ccatacgttc ctcaccgata cgaccagaat ccatcagaac ctgacgattc 60

<210> SEQ ID NO 225
<211> LENGTH: 60
<212> TYPE: DNA
<213> ORGANISM: Artificial Sequence
<220> FEATURE:
<223> OTHER INFORMATION: Synthesized

<400> SEQUENCE: 225
gaacgtatgg agactgcact gcaacatctg catcgtatca accctgagac tgaacttgaa 60

<210> SEQ ID NO 226
<211> LENGTH: 60
<212> TYPE: DNA
<213> ORGANISM: Artificial Sequence
<220> FEATURE:
<223> OTHER INFORMATION: Synthesized

<400> SEQUENCE: 226
aaggaccaga tgactcttca gtgatacgat gtgcatgacc ttcaagttca gtctcagggt 60

<210> SEQ ID NO 227
<211> LENGTH: 60
<212> TYPE: DNA
<213> ORGANISM: Artificial Sequence
<220> FEATURE:
<223> OTHER INFORMATION: Synthesized

<400> SEQUENCE: 227
tgaagagtca tctggtcctt gggttgaagc atctgacatc gtcattgatg cacgttacga 60

<210> SEQ ID NO 228
<211> LENGTH: 60
<212> TYPE: DNA
<213> ORGANISM: Artificial Sequence
<220> FEATURE:
<223> OTHER INFORMATION: Synthesized

<400> SEQUENCE: 228
acgaacacac agacgattca gtgcgtaacg ttcagggaag tcgtaacgtg catcaatgac 60

<210> SEQ ID NO 229
<211> LENGTH: 60
<212> TYPE: DNA
<213> ORGANISM: Artificial Sequence
<220> FEATURE:
<223> OTHER INFORMATION: Synthesized

<400> SEQUENCE: 229
tgaatcgtct gtgtgttcgt catggtcgtc caatgattga agctgccatg tatgcatacg 60

<210> SEQ ID NO 230
<211> LENGTH: 60
<212> TYPE: DNA

<213> ORGANISM: Artificial Sequence
<220> FEATURE:
<223> OTHER INFORMATION: Synthesized

<400> SEQUENCE: 230
caagcagtct taccagggtc gatagtcatc agtgagactt cgtatgcata catggcagct 60

<210> SEQ ID NO 231
<211> LENGTH: 60
<212> TYPE: DNA
<213> ORGANISM: Artificial Sequence
<220> FEATURE:
<223> OTHER INFORMATION: Synthesized

<400> SEQUENCE: 231
gaccctggta agactgcttg ccttgagtgt ctgtatcctg aaggtggtca gccttgggaa 60

<210> SEQ ID NO 232
<211> LENGTH: 60
<212> TYPE: DNA
<213> ORGANISM: Artificial Sequence
<220> FEATURE:
<223> OTHER INFORMATION: Synthesized

<400> SEQUENCE: 232
tcagaccaga ggttgcaccc aggacaggga aacccagtgg ttcccaaggc tgaccacctt 60

<210> SEQ ID NO 233
<211> LENGTH: 60
<212> TYPE: DNA
<213> ORGANISM: Artificial Sequence
<220> FEATURE:
<223> OTHER INFORMATION: Synthesized

<400> SEQUENCE: 233
gggtgcaacc tctggtctga ttggttgcat ggctgcactg gaagctgtca agtggatcac 60

<210> SEQ ID NO 234
<211> LENGTH: 60
<212> TYPE: DNA
<213> ORGANISM: Artificial Sequence
<220> FEATURE:
<223> OTHER INFORMATION: Synthesized

<400> SEQUENCE: 234
catacggtac atacgatcag tgaacagatt accagcatca gtgatccact tgacagcttc 60

<210> SEQ ID NO 235
<211> LENGTH: 60
<212> TYPE: DNA
<213> ORGANISM: Artificial Sequence
<220> FEATURE:
<223> OTHER INFORMATION: Synthesized

<400> SEQUENCE: 235
ctgatcgtat gtaccgtatg aacgttctgg acatgtcatc atgcactatc gctgtcaagc 60

<210> SEQ ID NO 236
<211> LENGTH: 60
<212> TYPE: DNA
<213> ORGANISM: Artificial Sequence
<220> FEATURE:
<223> OTHER INFORMATION: Synthesized

<400> SEQUENCE: 236
gtgtcaccac cagtaccaca gcatggacaa cgtgggttac gcttgacagc gatagtgcat 60

<210> SEQ ID NO 237
<211> LENGTH: 46
<212> TYPE: DNA
<213> ORGANISM: Artificial Sequence
<220> FEATURE:
<223> OTHER INFORMATION: Synthesized

<400> SEQUENCE: 237
attacaggta tgcaacagac tcatcagtgt caccaccagt accaca 46

<210> SEQ ID NO 238
<211> LENGTH: 60
<212> TYPE: DNA
<213> ORGANISM: Artificial Sequence
<220> FEATURE:
<223> OTHER INFORMATION: Synthesized

<400> SEQUENCE: 238
atgtctcgtc tgcacatctg tgatactaca cttcgtgatg gtgaacaggc acctggtgtt 60

<210> SEQ ID NO 239
<211> LENGTH: 60
<212> TYPE: DNA
<213> ORGANISM: Artificial Sequence
<220> FEATURE:
<223> OTHER INFORMATION: Synthesized

<400> SEQUENCE: 239
gcatgattgc aatctcggtc ttctcctcag cagagaatgc aacaccaggt gcctgttcac 60

<210> SEQ ID NO 240
<211> LENGTH: 60
<212> TYPE: DNA
<213> ORGANISM: Artificial Sequence
<220> FEATURE:
<223> OTHER INFORMATION: Synthesized

<400> SEQUENCE: 240
gaccgagatt gcaatcatgc tggattctgc tggtgtcgag caggctgaga tcggtattcc 60

<210> SEQ ID NO 241
<211> LENGTH: 60
<212> TYPE: DNA
<213> ORGANISM: Artificial Sequence
<220> FEATURE:
<223> OTHER INFORMATION: Synthesized

<400> SEQUENCE: 241
gatacgtgca atggaacggc actcagtctt acccattgca ggaataccga tctcagcctg 60

<210> SEQ ID NO 242
<211> LENGTH: 60
<212> TYPE: DNA
<213> ORGANISM: Artificial Sequence
<220> FEATURE:
<223> OTHER INFORMATION: Synthesized

<400> SEQUENCE: 242
gccgttccat tgcacgtatc gctgcactcg gtcttcagat gaagctcatg acttggaacc 60

<210> SEQ ID NO 243
<211> LENGTH: 60
<212> TYPE: DNA
<213> ORGANISM: Artificial Sequence
<220> FEATURE:

<223> OTHER INFORMATION: Synthesized

<400> SEQUENCE: 243
ccagtggatt cggttgcatc gatgtcggtg aagacagcac ggttccaagt catgagcttc 60

<210> SEQ ID NO 244
<211> LENGTH: 60
<212> TYPE: DNA
<213> ORGANISM: Artificial Sequence
<220> FEATURE:
<223> OTHER INFORMATION: Synthesized

<400> SEQUENCE: 244
gatgcaaccg aatccactgg tgttggttgg gcacacatct ctgtccctgt ctcaactgtc 60

<210> SEQ ID NO 245
<211> LENGTH: 60
<212> TYPE: DNA
<213> ORGANISM: Artificial Sequence
<220> FEATURE:
<223> OTHER INFORMATION: Synthesized

<400> SEQUENCE: 245
tgacctgttc agggttcata cccagcttag acttcatctg gacagttgag acagggacag 60

<210> SEQ ID NO 246
<211> LENGTH: 60
<212> TYPE: DNA
<213> ORGANISM: Artificial Sequence
<220> FEATURE:
<223> OTHER INFORMATION: Synthesized

<400> SEQUENCE: 246
tatgaaccct gaacaggtca ctgaactgat ccgtaagtcc gttgactatg cactgtgcaa 60

<210> SEQ ID NO 247
<211> LENGTH: 60
<212> TYPE: DNA
<213> ORGANISM: Artificial Sequence
<220> FEATURE:
<223> OTHER INFORMATION: Synthesized

<400> SEQUENCE: 247
acgtgatgca tcctcgaaac caacagagac agtcagaccc ttgcacagtg catagtcaac 60

<210> SEQ ID NO 248
<211> LENGTH: 60
<212> TYPE: DNA
<213> ORGANISM: Artificial Sequence
<220> FEATURE:
<223> OTHER INFORMATION: Synthesized

<400> SEQUENCE: 248
gtttcgagga tgcatcacgt gcagatgatc tgttccttga gcagttggca aaccagctct 60

<210> SEQ ID NO 249
<211> LENGTH: 60
<212> TYPE: DNA
<213> ORGANISM: Artificial Sequence
<220> FEATURE:
<223> OTHER INFORMATION: Synthesized

<400> SEQUENCE: 249
agagtatcag cgtaacggaa acgacggata ccatcacgat agagctggtt tgccaactgc 60

<210> SEQ ID NO 250
<211> LENGTH: 60
<212> TYPE: DNA
<213> ORGANISM: Artificial Sequence
<220> FEATURE:
<223> OTHER INFORMATION: Synthesized

<400> SEQUENCE: 250
ttccgttacg ctgatactct gtctgttcat caccctgctg caatcgctgc acgtatcgat 60

<210> SEQ ID NO 251
<211> LENGTH: 60
<212> TYPE: DNA
<213> ORGANISM: Artificial Sequence
<220> FEATURE:
<223> OTHER INFORMATION: Synthesized

<400> SEQUENCE: 251
ttccgttacg ctgatactct gtctgttcat caccctgctg caatcgctgc acgtatcgat 60

<210> SEQ ID NO 252
<211> LENGTH: 60
<212> TYPE: DNA
<213> ORGANISM: Artificial Sequence
<220> FEATURE:
<223> OTHER INFORMATION: Synthesized

<400> SEQUENCE: 252
acaggacgtc gaactggaga tccactgtca caacgactac ggtctggcac ttgccaacac 60

<210> SEQ ID NO 253
<211> LENGTH: 60
<212> TYPE: DNA
<213> ORGANISM: Artificial Sequence
<220> FEATURE:
<223> OTHER INFORMATION: Synthesized

<400> SEQUENCE: 253
ggttgatgcc caaacagcac cagcttgcag tgcagccaga gtgttggcaa gtgccagacc 60

<210> SEQ ID NO 254
<211> LENGTH: 60
<212> TYPE: DNA
<213> ORGANISM: Artificial Sequence
<220> FEATURE:
<223> OTHER INFORMATION: Synthesized

<400> SEQUENCE: 254
gtgctgtttg ggcatcaacc actgtctctg gtcttggtga acgtgctggt aacactgcac 60

<210> SEQ ID NO 255
<211> LENGTH: 60
<212> TYPE: DNA
<213> ORGANISM: Artificial Sequence
<220> FEATURE:
<223> OTHER INFORMATION: Synthesized

<400> SEQUENCE: 255
ccttggtaca gatcacgcca agacatgaca acctcctcca gtgcagtgtt accagcacgt 60

<210> SEQ ID NO 256
<211> LENGTH: 60
<212> TYPE: DNA
<213> ORGANISM: Artificial Sequence
<220> FEATURE:
<223> OTHER INFORMATION: Synthesized

```
<400> SEQUENCE: 256

tggcgtgatc tgtaccaagg tacttgctct gtccgtcctg aactgctgaa tccactggct     60


<210> SEQ ID NO 257
<211> LENGTH: 60
<212> TYPE: DNA
<213> ORGANISM: Artificial Sequence
<220> FEATURE:
<223> OTHER INFORMATION: Synthesized

<400> SEQUENCE: 257

cttcagggat gatacggttg gatgccttgg agaccagtgc agccagtgga ttcagcagtt     60


<210> SEQ ID NO 258
<211> LENGTH: 60
<212> TYPE: DNA
<213> ORGANISM: Artificial Sequence
<220> FEATURE:
<223> OTHER INFORMATION: Synthesized

<400> SEQUENCE: 258

caaccgtatc atccctgaag gtaagccaat cgttggtgac atggtcttcg cacatgaatc     60


<210> SEQ ID NO 259
<211> LENGTH: 60
<212> TYPE: DNA
<213> ORGANISM: Artificial Sequence
<220> FEATURE:
<223> OTHER INFORMATION: Synthesized

<400> SEQUENCE: 259

tgcagcacgt tccttcagca gaccattgat gtggatacca gattcatgtg cgaagaccat     60


<210> SEQ ID NO 260
<211> LENGTH: 60
<212> TYPE: DNA
<213> ORGANISM: Artificial Sequence
<220> FEATURE:
<223> OTHER INFORMATION: Synthesized

<400> SEQUENCE: 260

tgctgaagga acgtgctgca taccaggcac ttgacccaac tgaactgggt actgaccact     60


<210> SEQ ID NO 261
<211> LENGTH: 60
<212> TYPE: DNA
<213> ORGANISM: Artificial Sequence
<220> FEATURE:
<223> OTHER INFORMATION: Synthesized

<400> SEQUENCE: 261

tggacagcag aacgaccaga gtgcttacca aggacgaatg agtggtcagt acccagttca     60


<210> SEQ ID NO 262
<211> LENGTH: 60
<212> TYPE: DNA
<213> ORGANISM: Artificial Sequence
<220> FEATURE:
<223> OTHER INFORMATION: Synthesized

<400> SEQUENCE: 262

tctggtcgtt ctgctgtcca gtacatgctg gaacaggaag gtatcgaggc tggctctggt     60


<210> SEQ ID NO 263
<211> LENGTH: 60
```

<212> TYPE: DNA
<213> ORGANISM: Artificial Sequence
<220> FEATURE:
<223> OTHER INFORMATION: Synthesized

<400> SEQUENCE: 263
caccaaccag acgaagacgt tcaagcagga acttgatctc accagagcca gcctcgatac 60

<210> SEQ ID NO 264
<211> LENGTH: 60
<212> TYPE: DNA
<213> ORGANISM: Artificial Sequence
<220> FEATURE:
<223> OTHER INFORMATION: Synthesized

<400> SEQUENCE: 264
acgtcttcgt ctggttggtg aagaccctaa gcgtgtcatc cattctgctg acttgcgtcg 60

<210> SEQ ID NO 265
<211> LENGTH: 57
<212> TYPE: DNA
<213> ORGANISM: Artificial Sequence
<220> FEATURE:
<223> OTHER INFORMATION: Synthesized

<400> SEQUENCE: 265
ttacttaggc agttcagcag ggtagtactg gagccaacga cgcaagtcag cagaatg 57

<210> SEQ ID NO 266
<211> LENGTH: 24
<212> TYPE: DNA
<213> ORGANISM: Artificial Sequence
<220> FEATURE:
<223> OTHER INFORMATION: Synthesized

<400> SEQUENCE: 266
atcttcgtca acatggtgga gcac 24

<210> SEQ ID NO 267
<211> LENGTH: 23
<212> TYPE: DNA
<213> ORGANISM: Artificial Sequence
<220> FEATURE:
<223> OTHER INFORMATION: Synthesized

<400> SEQUENCE: 267
caagcttggt cgacaattcc cga 23

<210> SEQ ID NO 268
<211> LENGTH: 34
<212> TYPE: DNA
<213> ORGANISM: Artificial Sequence
<220> FEATURE:
<223> OTHER INFORMATION: Synthesized

<400> SEQUENCE: 268
cggaattcct cgagatcttc gtcaacatgg tgga 34

<210> SEQ ID NO 269
<211> LENGTH: 41
<212> TYPE: DNA
<213> ORGANISM: Artificial Sequence
<220> FEATURE:
<223> OTHER INFORMATION: Synthesized

<400> SEQUENCE: 269
gcaagcttgg tcgacaattc ccgatctagt aacatagatg a 41

<210> SEQ ID NO 270
<211> LENGTH: 48
<212> TYPE: DNA
<213> ORGANISM: Artificial Sequence
<220> FEATURE:
<223> OTHER INFORMATION: Synthesized

<400> SEQUENCE: 270
cattacaatt acatttacaa ttaccaatgc gtcagattgc attctacg 48

<210> SEQ ID NO 271
<211> LENGTH: 48
<212> TYPE: DNA
<213> ORGANISM: Artificial Sequence
<220> FEATURE:
<223> OTHER INFORMATION: Synthesized

<400> SEQUENCE: 271
cgtagaatgc aatctgacgc attggtaatt gtaaatgtaa ttgtaatg 48

<210> SEQ ID NO 272
<211> LENGTH: 43
<212> TYPE: DNA
<213> ORGANISM: Artificial Sequence
<220> FEATURE:
<223> OTHER INFORMATION: Synthesized

<400> SEQUENCE: 272
aggctgaggc atctggtcag taagatcgtt caaacatttg gca 43

<210> SEQ ID NO 273
<211> LENGTH: 43
<212> TYPE: DNA
<213> ORGANISM: Artificial Sequence
<220> FEATURE:
<223> OTHER INFORMATION: Synthesized

<400> SEQUENCE: 273
tgccaaatgt ttgaacgatc ttactgacca gatgcctcag cct 43

<210> SEQ ID NO 274
<211> LENGTH: 47
<212> TYPE: DNA
<213> ORGANISM: Artificial Sequence
<220> FEATURE:
<223> OTHER INFORMATION: Synthesized

<400> SEQUENCE: 274
cattacaatt actatttaca attaccatgt catcaatcgt tgacaag 47

<210> SEQ ID NO 275
<211> LENGTH: 47
<212> TYPE: DNA
<213> ORGANISM: Artificial Sequence
<220> FEATURE:
<223> OTHER INFORMATION: Synthesized

<400> SEQUENCE: 275
cttgtcaacg attgatgaca tggtaattgt aaatagtaat tgtaatg 47

<210> SEQ ID NO 276
<211> LENGTH: 42
<212> TYPE: DNA
<213> ORGANISM: Artificial Sequence
<220> FEATURE:
<223> OTHER INFORMATION: Synthesized

<400> SEQUENCE: 276
gactgctgag gttcctgtct aagatcgttc aaacatttgg ca 42

<210> SEQ ID NO 277
<211> LENGTH: 42
<212> TYPE: DNA
<213> ORGANISM: Artificial Sequence
<220> FEATURE:
<223> OTHER INFORMATION: Synthesized

<400> SEQUENCE: 277
tgccaaatgt ttgaacgatc ttagacagga acctcagcag tc 42

<210> SEQ ID NO 278
<211> LENGTH: 48
<212> TYPE: DNA
<213> ORGANISM: Artificial Sequence
<220> FEATURE:
<223> OTHER INFORMATION: Synthesized

<400> SEQUENCE: 278
cattacaatt actatttaca attaccatgt ctgaacgtcc taacattg 48

<210> SEQ ID NO 279
<211> LENGTH: 48
<212> TYPE: DNA
<213> ORGANISM: Artificial Sequence
<220> FEATURE:
<223> OTHER INFORMATION: Synthesized

<400> SEQUENCE: 279
caatgttagg acgttcagac atggtaattg taaatagtaa ttgtaatg 48

<210> SEQ ID NO 280
<211> LENGTH: 42
<212> TYPE: DNA
<213> ORGANISM: Artificial Sequence
<220> FEATURE:
<223> OTHER INFORMATION: Synthesized

<400> SEQUENCE: 280
ctccttcgac ctggttcgtt aagatcgttc aaacatttgg ca 42

<210> SEQ ID NO 281
<211> LENGTH: 42
<212> TYPE: DNA
<213> ORGANISM: Artificial Sequence
<220> FEATURE:
<223> OTHER INFORMATION: Synthesized

<400> SEQUENCE: 281
tgccaaatgt ttgaacgatc ttaacgaacc aggtcgaagg ag 42

<210> SEQ ID NO 282
<211> LENGTH: 48
<212> TYPE: DNA
<213> ORGANISM: Artificial Sequence
<220> FEATURE:
<223> OTHER INFORMATION: Synthesized

<400> SEQUENCE: 282
cattacaatt acatttacaa ttaccatgga ctcacttgct gatctctc 48

<210> SEQ ID NO 283
<211> LENGTH: 48
<212> TYPE: DNA
<213> ORGANISM: Artificial Sequence
<220> FEATURE:
<223> OTHER INFORMATION: Synthesized

<400> SEQUENCE: 283
gagagatcag caagtgagtc catggtaatt gtaaatgtaa ttgtaatg 48

<210> SEQ ID NO 284
<211> LENGTH: 43
<212> TYPE: DNA
<213> ORGANISM: Artificial Sequence
<220> FEATURE:
<223> OTHER INFORMATION: Synthesized

<400> SEQUENCE: 284
ctatcgaaca cttcggtggt taagatcgtt caaacatttg gca 43

<210> SEQ ID NO 285
<211> LENGTH: 43
<212> TYPE: DNA
<213> ORGANISM: Artificial Sequence
<220> FEATURE:
<223> OTHER INFORMATION: Synthesized

<400> SEQUENCE: 285
tgccaaatgt ttgaacgatc ttaaccaccg aagtgttcga tag 43

<210> SEQ ID NO 286
<211> LENGTH: 48
<212> TYPE: DNA
<213> ORGANISM: Artificial Sequence
<220> FEATURE:
<223> OTHER INFORMATION: Synthesized

<400> SEQUENCE: 286
cattacaatt actatttaca attaccatgg aaccagctgt ctccaatg 48

<210> SEQ ID NO 287
<211> LENGTH: 48
<212> TYPE: DNA
<213> ORGANISM: Artificial Sequence
<220> FEATURE:
<223> OTHER INFORMATION: Synthesized

<400> SEQUENCE: 287
cattggagac agctggttcc atggtaattg taaatagtaa ttgtaatg 48

<210> SEQ ID NO 288
<211> LENGTH: 43
<212> TYPE: DNA
<213> ORGANISM: Artificial Sequence
<220> FEATURE:
<223> OTHER INFORMATION: Synthesized

<400> SEQUENCE: 288
aggagactga gttcgctgac taagatcgtt caaacatttg gca 43

<210> SEQ ID NO 289
<211> LENGTH: 43
<212> TYPE: DNA
<213> ORGANISM: Artificial Sequence
<220> FEATURE:
<223> OTHER INFORMATION: Synthesized

<400> SEQUENCE: 289
tgccaaatgt ttgaacgatc ttagtcagcg aactcagtct cct 43

<210> SEQ ID NO 290
<211> LENGTH: 48
<212> TYPE: DNA
<213> ORGANISM: Artificial Sequence
<220> FEATURE:
<223> OTHER INFORMATION: Synthesized

<400> SEQUENCE: 290
cattacaatt actatttaca attaccatgc ttatcaagtc tgcaacca 48

<210> SEQ ID NO 291
<211> LENGTH: 48
<212> TYPE: DNA
<213> ORGANISM: Artificial Sequence
<220> FEATURE:
<223> OTHER INFORMATION: Synthesized

<400> SEQUENCE: 291
tggttgcaga cttgataagc atggtaattg taaatagtaa ttgtaatg 48

<210> SEQ ID NO 292
<211> LENGTH: 41
<212> TYPE: DNA
<213> ORGANISM: Artificial Sequence
<220> FEATURE:
<223> OTHER INFORMATION: Synthesized

<400> SEQUENCE: 292
gaacgtggtc gtggtggtta agatcgttca aacatttggc a 41

<210> SEQ ID NO 293
<211> LENGTH: 41
<212> TYPE: DNA
<213> ORGANISM: Artificial Sequence
<220> FEATURE:
<223> OTHER INFORMATION: Synthesized

<400> SEQUENCE: 293
tgccaaatgt ttgaacgatc ttaaccacca cgaccacgtt c 41

<210> SEQ ID NO 294
<211> LENGTH: 47
<212> TYPE: DNA
<213> ORGANISM: Artificial Sequence
<220> FEATURE:
<223> OTHER INFORMATION: Synthesized

<400> SEQUENCE: 294
cattacaatt actatttaca attaccatga aggttgcatt cgcaact 47

<210> SEQ ID NO 295
<211> LENGTH: 47
<212> TYPE: DNA
<213> ORGANISM: Artificial Sequence
<220> FEATURE:
<223> OTHER INFORMATION: Synthesized

<400> SEQUENCE: 295
agttgcgaat gcaaccttca tggtaattgt aaatagtaat tgtaatg 47

<210> SEQ ID NO 296

<211> LENGTH: 41
<212> TYPE: DNA
<213> ORGANISM: Artificial Sequence
<220> FEATURE:
<223> OTHER INFORMATION: Synthesized

<400> SEQUENCE: 296
tctggtaagg ctgagtcata agatcgttca aacatttggc a 41

<210> SEQ ID NO 297
<211> LENGTH: 41
<212> TYPE: DNA
<213> ORGANISM: Artificial Sequence
<220> FEATURE:
<223> OTHER INFORMATION: Synthesized

<400> SEQUENCE: 297
tctggtaagg ctgagtcata agatcgttca aacatttggc a 41

<210> SEQ ID NO 298
<211> LENGTH: 49
<212> TYPE: DNA
<213> ORGANISM: Artificial Sequence
<220> FEATURE:
<223> OTHER INFORMATION: Synthesized

<400> SEQUENCE: 298
cattacaatt actatttaca attaccatgg ttcaacttct tgaagattc 49

<210> SEQ ID NO 299
<211> LENGTH: 49
<212> TYPE: DNA
<213> ORGANISM: Artificial Sequence
<220> FEATURE:
<223> OTHER INFORMATION: Synthesized

<400> SEQUENCE: 299
gaatcttcaa gaagttgaac catggtaatt gtaaatagta attgtaatg 49

<210> SEQ ID NO 300
<211> LENGTH: 43
<212> TYPE: DNA
<213> ORGANISM: Artificial Sequence
<220> FEATURE:
<223> OTHER INFORMATION: Synthesized

<400> SEQUENCE: 300
atgagtctgt tgcatacctg taagatcgtt caaacatttg gca 43

<210> SEQ ID NO 301
<211> LENGTH: 43
<212> TYPE: DNA
<213> ORGANISM: Artificial Sequence
<220> FEATURE:
<223> OTHER INFORMATION: Synthesized

<400> SEQUENCE: 301
tgccaaatgt ttgaacgatc ttacaggtat gcaacagact cat 43

<210> SEQ ID NO 302
<211> LENGTH: 49
<212> TYPE: DNA
<213> ORGANISM: Artificial Sequence
<220> FEATURE:
<223> OTHER INFORMATION: Synthesized

<400> SEQUENCE: 302

```
cattacaatt actatttaca attaccatgt ctcgtctgca catctgtga              49


<210> SEQ ID NO 303
<211> LENGTH: 49
<212> TYPE: DNA
<213> ORGANISM: Artificial Sequence
<220> FEATURE:
<223> OTHER INFORMATION: Synthesized

<400> SEQUENCE: 303

tcacagatgt gcagacgaga catggtaatt gtaaatagta attgtaatg              49


<210> SEQ ID NO 304
<211> LENGTH: 43
<212> TYPE: DNA
<213> ORGANISM: Artificial Sequence
<220> FEATURE:
<223> OTHER INFORMATION: Synthesized

<400> SEQUENCE: 304

accctgctga actgcctaag taagatcgtt caaacatttg gca                    43


<210> SEQ ID NO 305
<211> LENGTH: 43
<212> TYPE: DNA
<213> ORGANISM: Artificial Sequence
<220> FEATURE:
<223> OTHER INFORMATION: Synthesized

<400> SEQUENCE: 305

tgccaaatgt ttgaacgatc ttacttaggc agttcagcag ggt                    43
```